United States Patent
Dahl et al.

(10) Patent No.: US 6,843,851 B2
(45) Date of Patent: Jan. 18, 2005

(54) COMPOSITIONS COMPRISING PENTAMANTANES AND PROCESSES FOR THEIR SEPARATION

(75) Inventors: Jeremy E. Dahl, Palo Alto, CA (US); Robert M. Carlson, Petaluma, CA (US)

(73) Assignee: Chevron U.S.A., Inc., San Ramon, CA (US)

(*) Notice: Subject to any disclaimer, the term of this patent is extended or adjusted under 35 U.S.C. 154(b) by 33 days.

(21) Appl. No.: 10/012,333

(22) Filed: Dec. 12, 2001

(65) Prior Publication Data

US 2002/0134301 A1 Sep. 26, 2002

Related U.S. Application Data

(60) Provisional application No. 60/262,842, filed on Jan. 19, 2001, and provisional application No. 60/307,063, filed on Jul. 20, 2001.

(51) Int. Cl.[7] .............................................. C30B 21/02
(52) U.S. Cl. ....................... 117/68; 117/69; 117/70; 23/295 R; 585/21; 585/800; 585/801; 585/812; 585/820
(58) Field of Search .......................... 117/68, 69, 70; 422/245.1; 23/295 R; 585/21, 800, 801, 812, 820

(56) References Cited

U.S. PATENT DOCUMENTS

| | | | |
|---|---|---|---|
| 3,457,318 A | 7/1969 | Capaldi | |
| 3,832,332 A | 8/1974 | Thompson | |
| 4,952,748 A | 8/1990 | Alexander | |
| 4,952,749 A | 8/1990 | Alexander | |
| 4,952,757 A | 8/1990 | Purcell et al. | |
| 4,982,049 A | 1/1991 | Alexander | |
| 5,017,734 A | 5/1991 | Baum | |
| 5,019,665 A | 5/1991 | Partridge | |
| 5,245,104 A | 9/1993 | Cullick | |
| 5,268,513 A | 12/1993 | Shen | |
| 5,298,666 A | 3/1994 | Shen | |
| 5,306,851 A | 4/1994 | Wu | |
| 5,347,063 A | 9/1994 | Shen | |
| 5,369,213 A | 11/1994 | Shen | |
| 5,380,947 A | 1/1995 | Chen | |
| 5,382,684 A | 1/1995 | Moini | |
| 5,397,488 A | 3/1995 | Chen | |
| 5,410,092 A | 4/1995 | Shen | |
| 5,414,189 A * | 5/1995 | Chen et al. ................. | 585/801 |
| 5,430,193 A | 7/1995 | Shen | |
| 5,461,184 A | 10/1995 | Swanson | |
| 5,498,812 A | 3/1996 | Bradway | |
| 5,576,355 A | 11/1996 | Chen | |
| 6,235,851 B1 | 5/2001 | Ishii | |
| 2002/0188163 A1 * | 12/2002 | Dahl et al. ................. | 585/800 |
| 2002/0193648 A1 * | 12/2002 | Dahl et al. .................... | 585/21 |

FOREIGN PATENT DOCUMENTS

| | | |
|---|---|---|
| EP | 0399851 | 11/1996 |
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", *Fuel*, vol. 58, pp. 228–230, (Mar. 1979).

(List continued on next page.)

*Primary Examiner*—Robert Kunemund
(74) *Attorney, Agent, or Firm*—Burns Doane Swecker & Mathis, L.L.P.

(57) ABSTRACT

Disclosed are compositions comprising one or more pentamantanes. Specifically disclosed are compositions comprising 10 to 100 weight percent of one or more pentamantanes. Also disclosed are novel processes for the separation and isolation of pentamantane components into recoverable fractions from a feedstock containing at least a higher diamondoid component which contains one or more pentamantane components.

51 Claims, 39 Drawing Sheets

OTHER PUBLICATIONS

Balaban, et al., Systemic Classification and Nomenclature of Diamond Hydrocarbons–I, *Tetrahedron*, 34, pp. 3599–3606, (1978).

Badziag, P., et al., "Nanometre–sized Diamonds are More Stable than Graphite", *Nature*, vol. 343, pp. 244–245, and 517.

Bagrii, Ye, et al., "Catalytic Breakdown of Paraffinic Hydrocarbons in the Presence of Adamantanes", *Petrol. Chem USSR*, vol. 30, No. 2, pp. 131–134, (1990).

Chung, et al., Recent Development in High–Energy Density Liquid Fuels, *Energy and Fuels*, 13, pp. 641–649, (1999).

Dahl, J., et al., Diamondoid Hydrocarbons as Indicators of Natural Oil Cracking, *Nature*, 399, pp. 54–57, (1999).

Drexler, Eric K., *Nanosystems: Molecular Machinary Manufacturing and Computation*, John Wiley & Sons, pp. 238–249, (1992).

Fort, Jr., et al., Adamantane: Consequences of the Diamondoid Structure, *Chem. Rev.*, 64, pp. 277–30, (1964).

Hala, V.S., et al., "Analyse Unds erwendung on Pyrolyseol", *Jahrgang*, pp. 85–87, (Feb. 1971) In German– English Abstract on p. 85.

Landa, S., "Adamantane and Its Homologues", *Current Science*, Gangalore, India, Vo. 32, pp. 485–489 (1963).

Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, *Fuel*, 74:10, pp. 1512–1521, (1995).

McKervey, Synthetic Approaches to Large Diamondoid Hydrocarbonds, *Tetrahedron*, 36, pp. 971–992, (1980).

Machacek, V., et al., "Let Od Objeveni Adamantanu", *Chemicke Listy/svazek*, pp. 753–761, (1982) Russian—English Abstract on p. 761.

Oya, A, et al., "Carbonization of Adamantanes to a Graphitizable Carbon", *Fuel*, vol. 60, pp. 667–669, (Aug. 1981).

Petrov, A., "Hydrocarbons of Adamantane Series as Indicies of Petroleum Catagenesis Process", *Advances in Organic Geo Chemistry*, 6th International Meeting on Organic Geochemistry, pp. 517–522 (1973).

Prusova, D., Liquid Chromatography of Adamantanes and Carbon Adsorbents, *J. Chrom*, 234, pp. 1–11, (1982).

Rollman, L., et al., "Adamantanes From Petroleum, with Zeolites", American Chemical Study, 210th ACS National Meeting, Abstract and paper, Aug. 20, 1995).

Sandia National Laboratories (2000), World's First Diamond Micromachines Created at Sandia, Press Release, (Feb. 22, 2000), www.Sandia.gov.

Schleyer, P., et al., "Nonacyclo[$11.7.1.1^{2,18}.0^{3,16}.0^{4,13}.0^{5,10}.0^{6,14}.0^{7,11}.0^{15,20}$]–Docosane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.*, vol. 114, No. 2, pp. 497–505, (1992).

Supryadkina, NY, et al., "Catalytic Dealkylation of Alkyladamantanes", *Petrol. Chem., USSR*, vol. 28, No. 2, pp. 103–110, (1988).

Tominaga, K., et al., "Next–generation Fine Chemicals Raw Material–Adamantane", *Chem Econ & Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom*, 270, pp. 199–205, (1983).

Wingert, W., "G.c.–m.s. Analysis of Diamondoid Hydrocarbons in Smackover Petroleums", *Fuel*, vol. 71, pp. 37–42, (Jan. 1992).

* cited by examiner

[1213]   [1234]   [12(1)3]

[1212]   [1(2,3)4]   [1231]   [12(3)4]

* Mirror plane indicating enantiomeric pair of pentamantanes

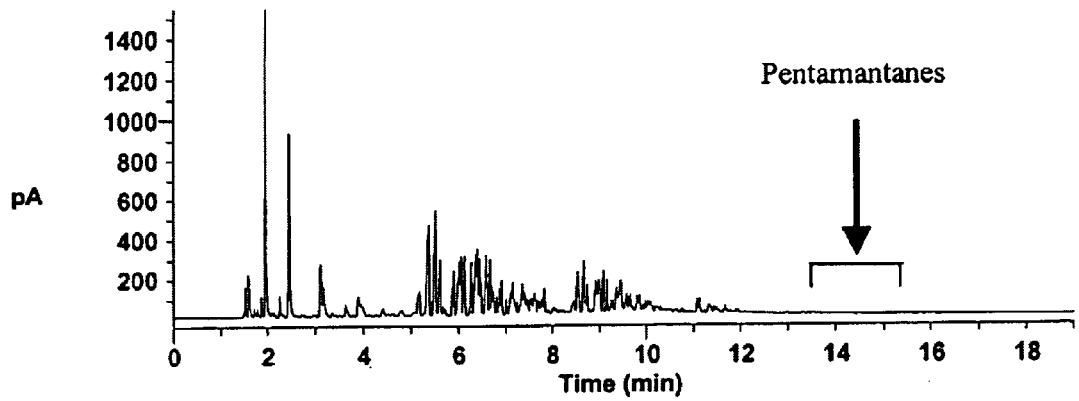
*FIG. 4*
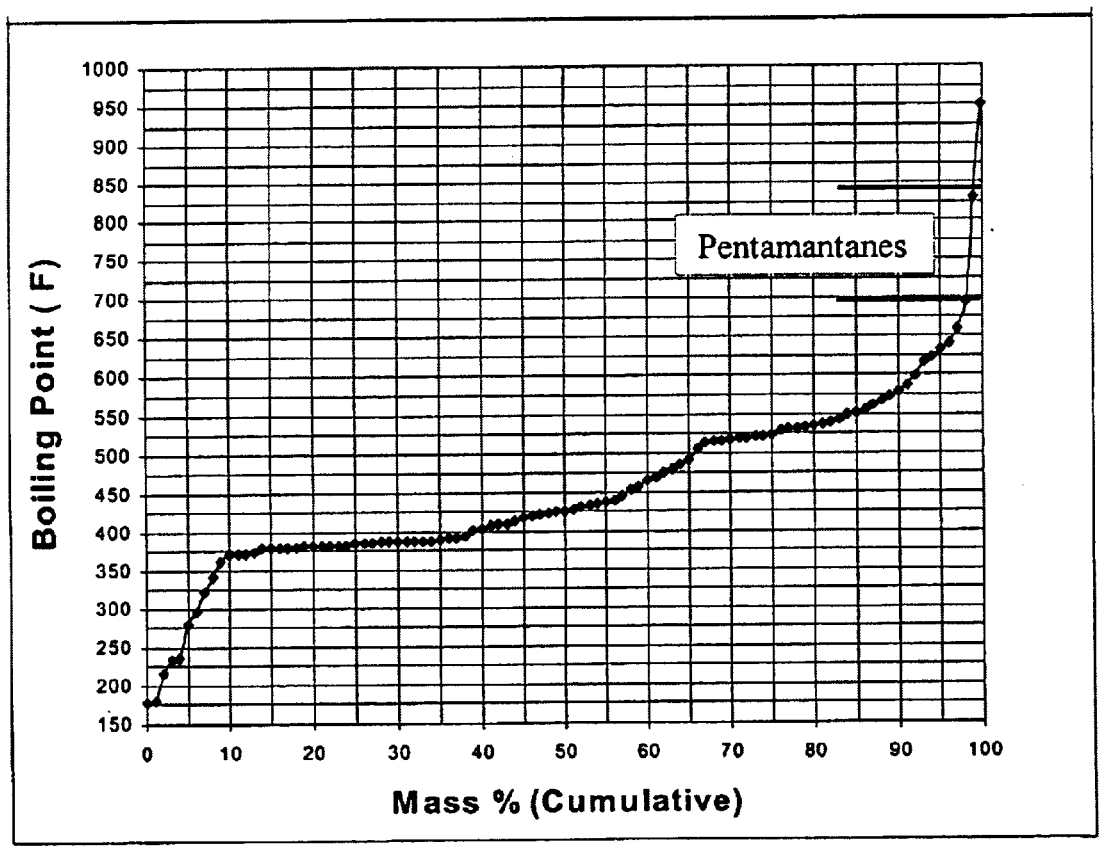

FIG. 7
A)
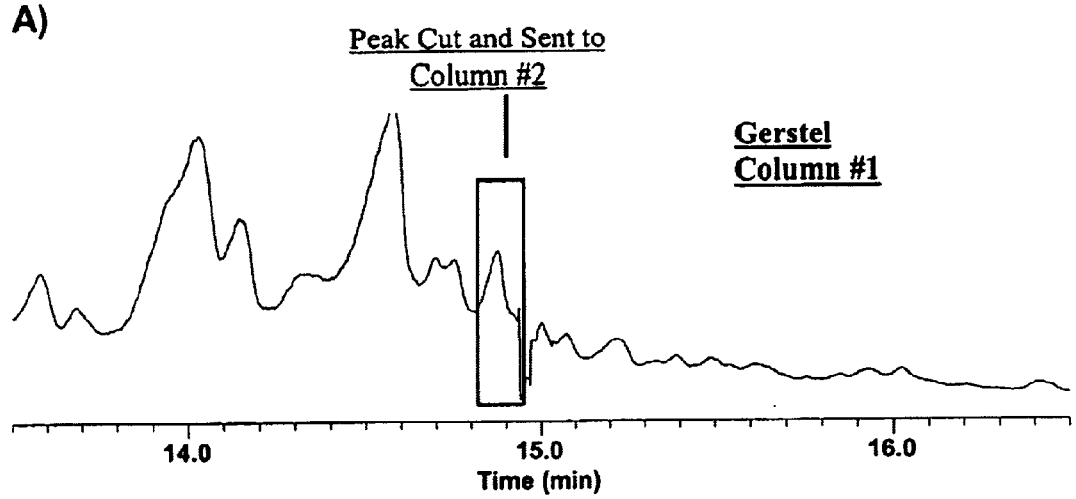
Peak Cut and Sent to Column #2
Gerstel Column #1
B)
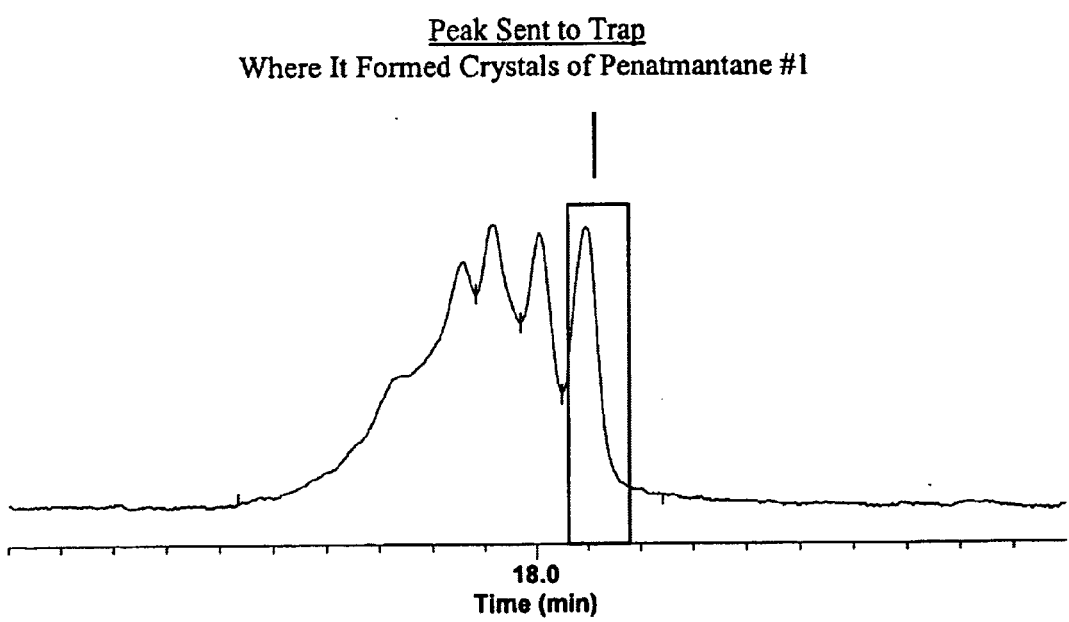
Gerstel Column #2
Peak Sent to Trap
Where It Formed Crystals of Penatmantane #1

FIG. 8
A.
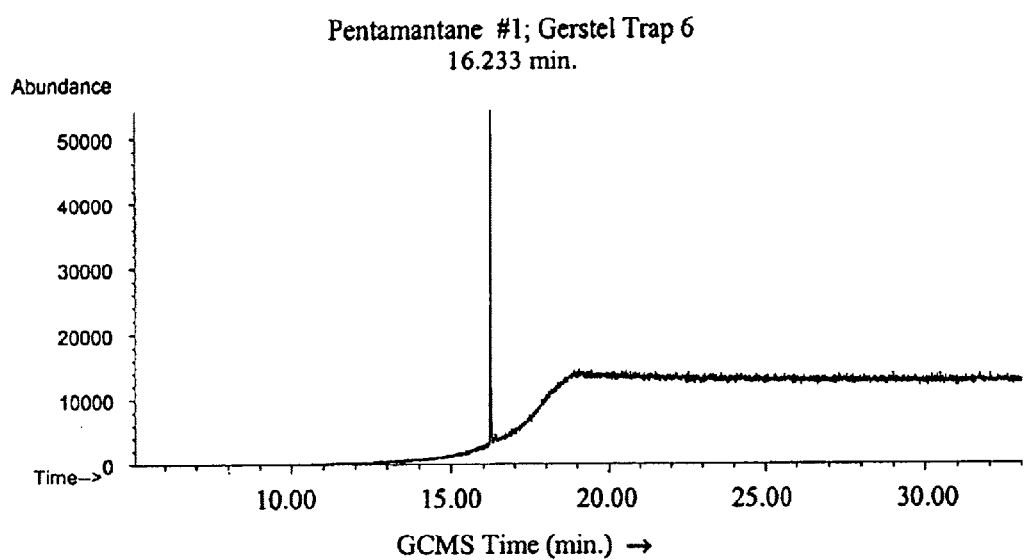
B.
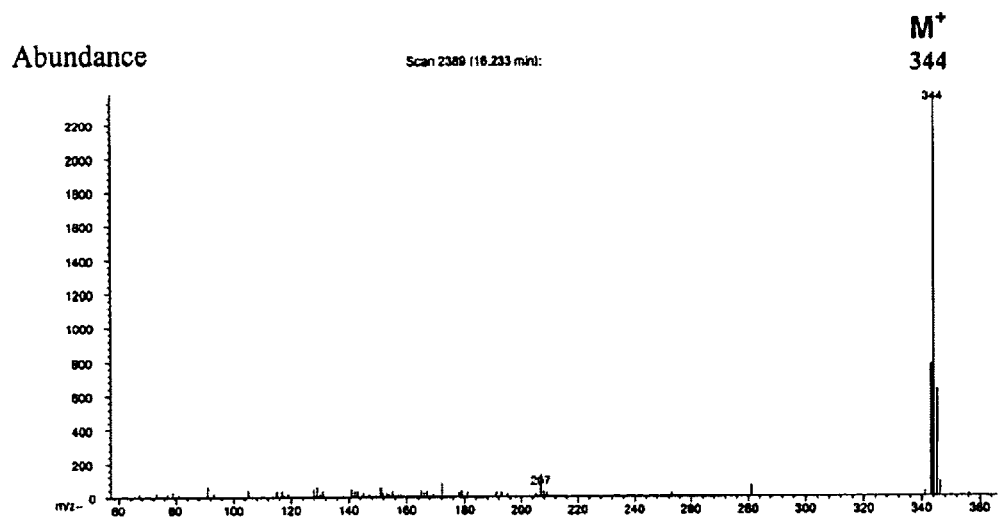

FIG. 9
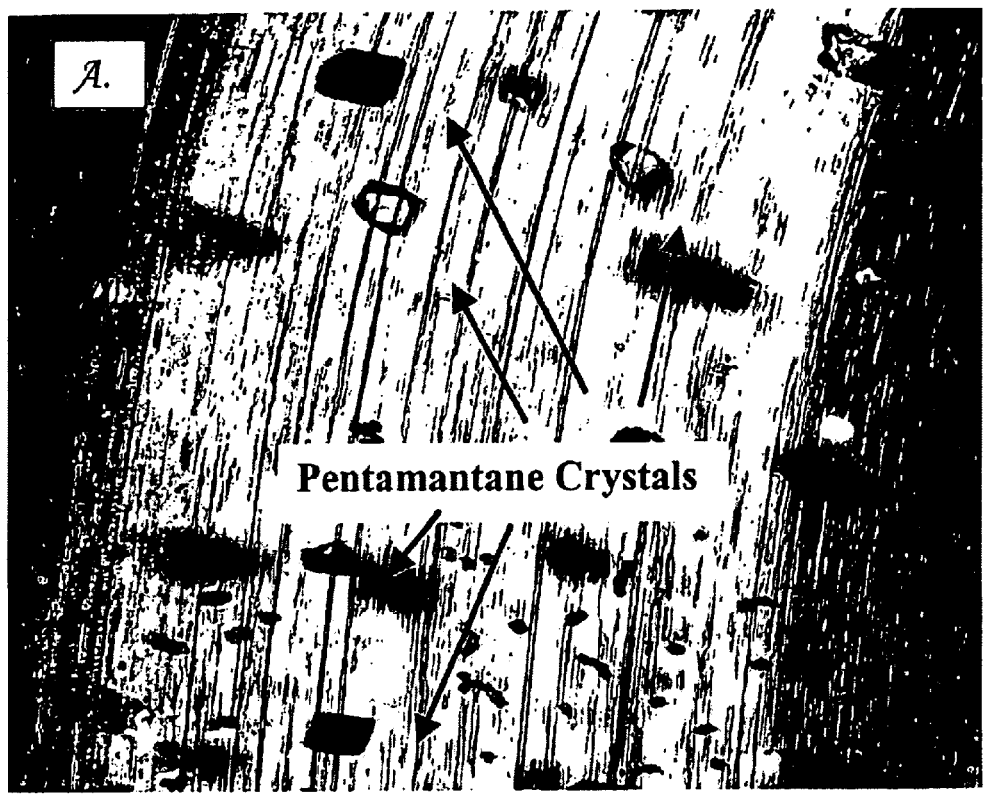
Isolated and Crystallized Pentamantanes
(2 of 10 possible)
(Crystal is approximately 250 microns in diameter)

FIG. 11
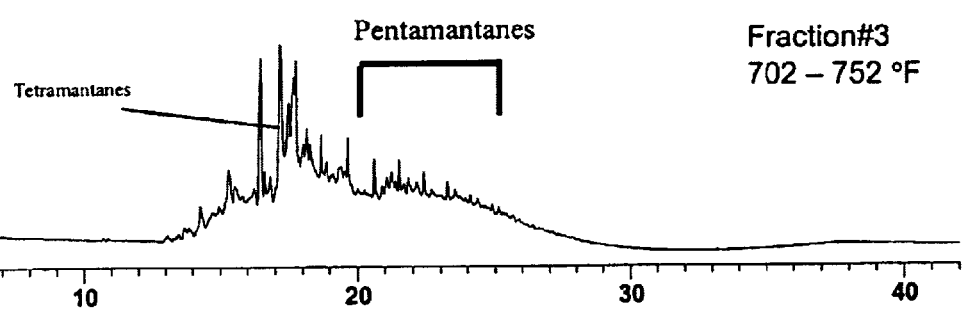
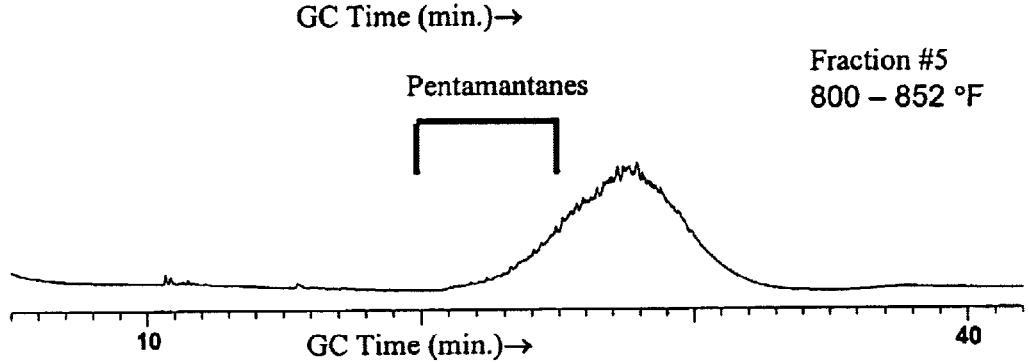

FIG. 12
A.
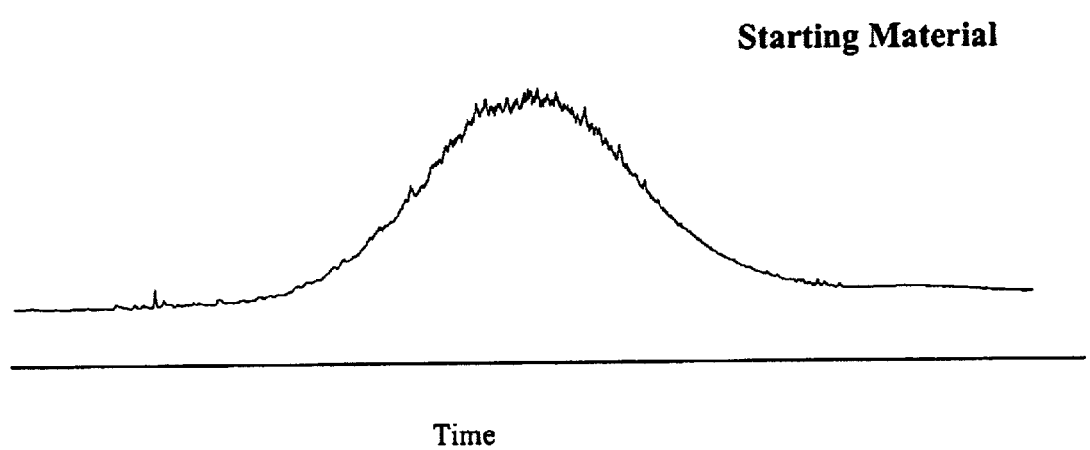
Starting Material
Time
B.
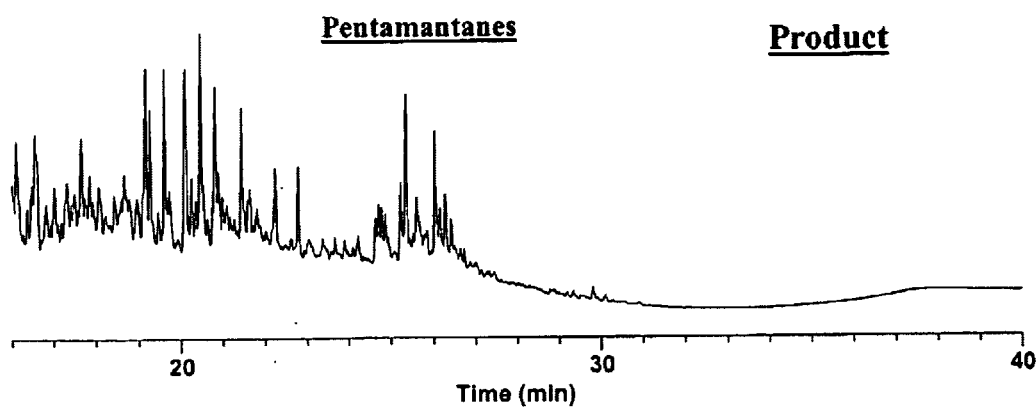
Pentamantanes    Product
Time (min)

FIG. 14

Pentamantane

| Hypercarb HPLC Fraction # | 1 | 2 | 3 | 4 | 5 | 6 | |
|---|---|---|---|---|---|---|---|
| 1 | | | | | | | |
| 2 | | | | | | | |
| 3 | | | | | | | |
| 4 | | | | | x | | Penta 5 |
| 5 | | | | | | | |
| 6 | | | | | | | |
| 7 | | | | | | | |
| 8 | | | | | | | |
| 9 | | | | | | ■ | Penta 6 |
| 10 | | | | | | x | |
| 11 | ■ | | | | | | Penta 1 |
| 12 | x | | | | | | |
| 13 | ■ | | | ■ | | | Penta 4 |
| 14 | | | | x | | | |
| 15 | | ■ | | ■ | | | Penta 2 |
| 16 | | x | | | | | |
| 17 | | ■ | | | | | |
| 35 | | | | | | | |
| 36 | | | | | | | |
| 37 | | | ■ | | | | Penta 3 |
| 38 | | | x | | | | |
| 39 | | | ■ | | | | |
| 40 | | | ■ | | | | |
| 41 | | | ■ | | | | |
| 42 | | | ■ | | | | |
| 43 | | | ■ | | | | |

Data from HPLC 19

FIG. 16
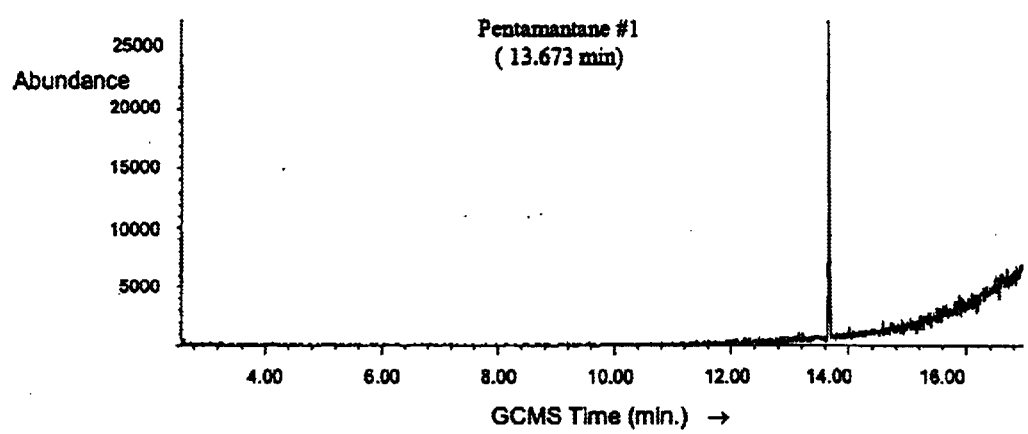
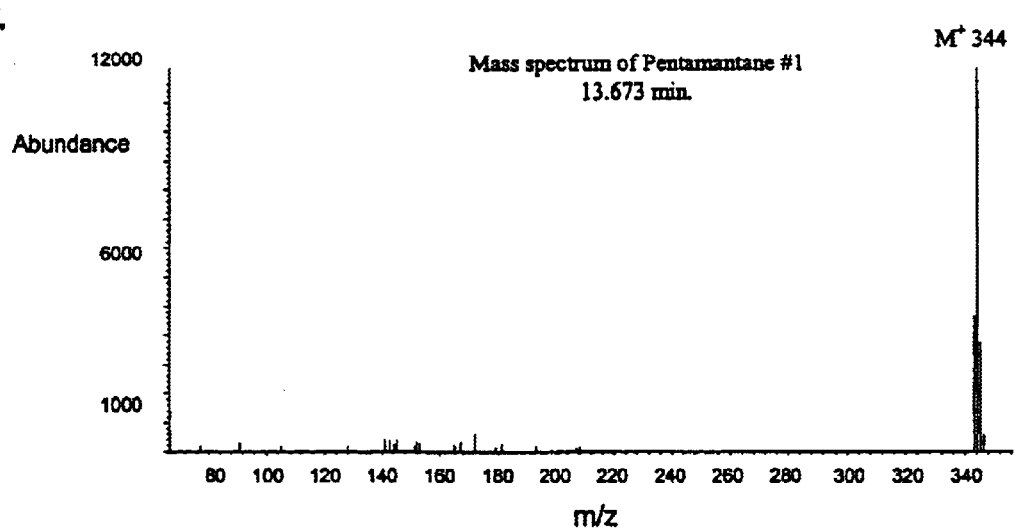

FIG. 17
A.
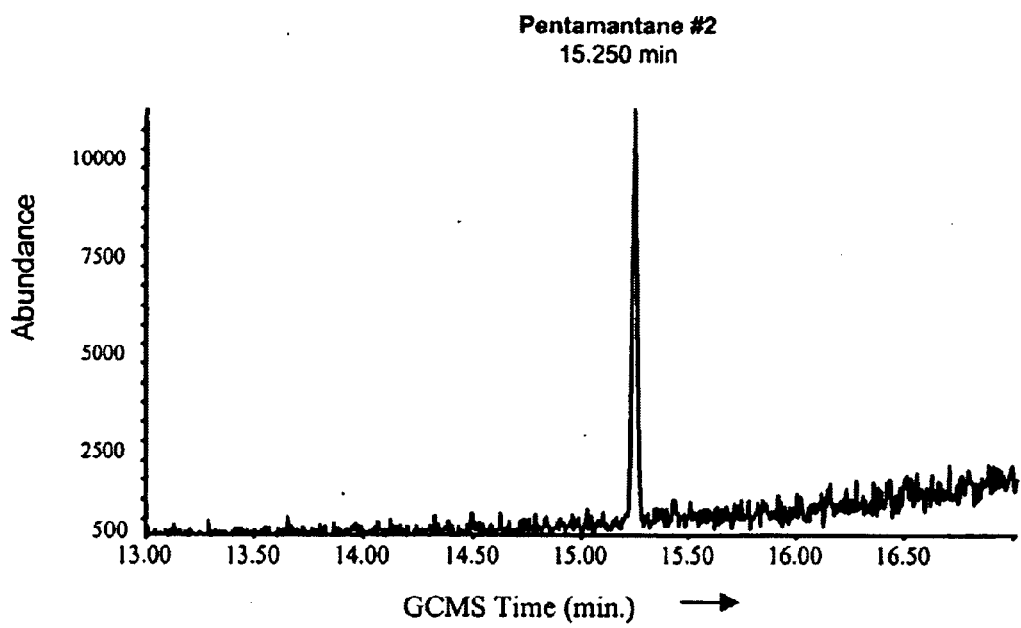
B.
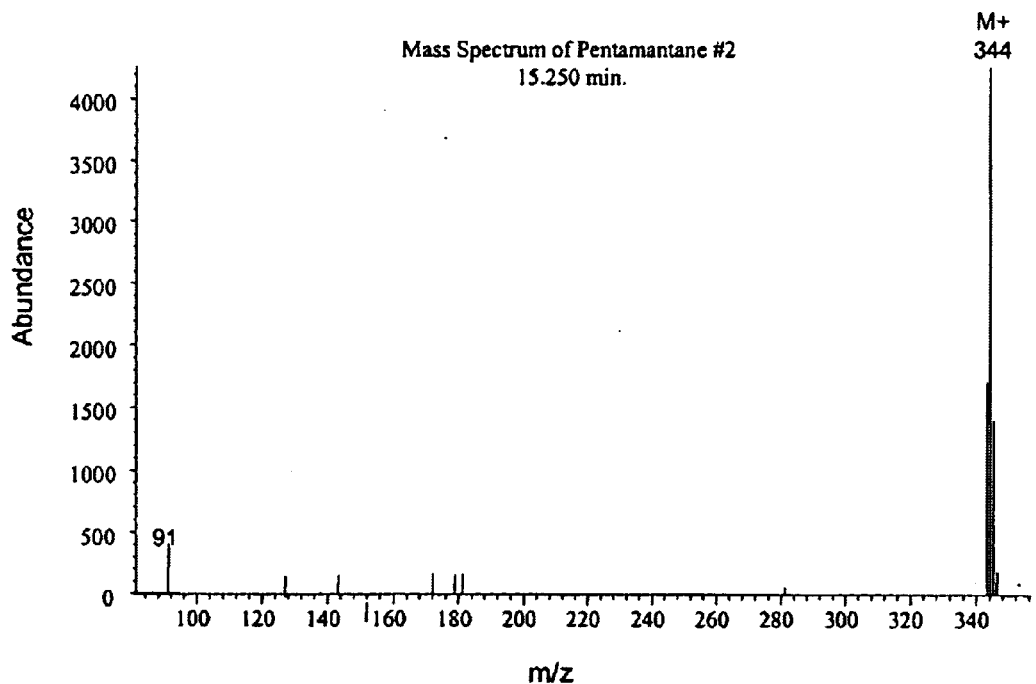

FIG. 18
𝓐..
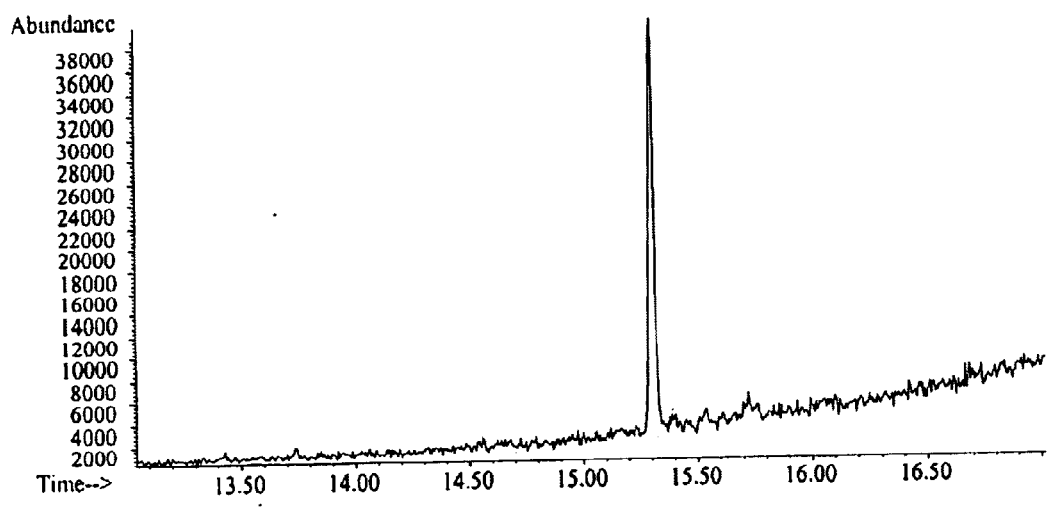
𝓑.
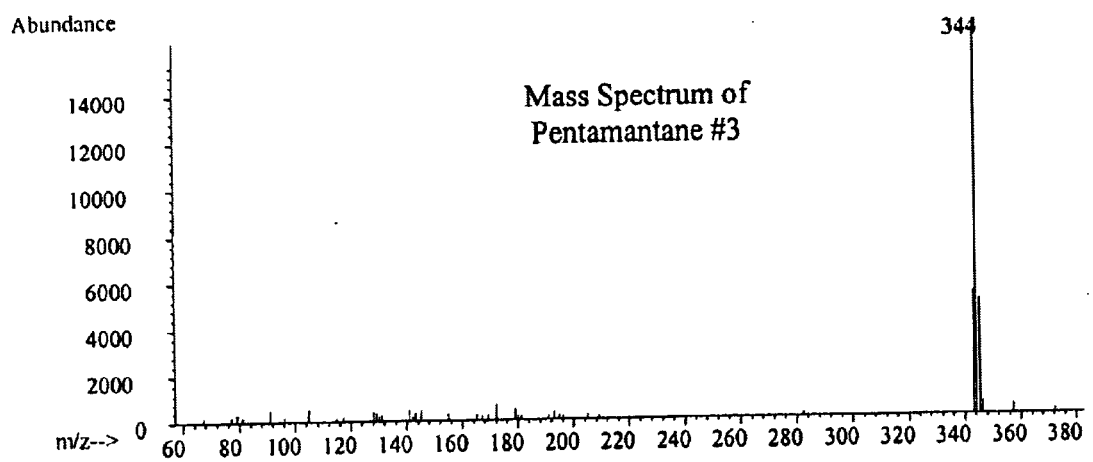

FIG. 19
A.
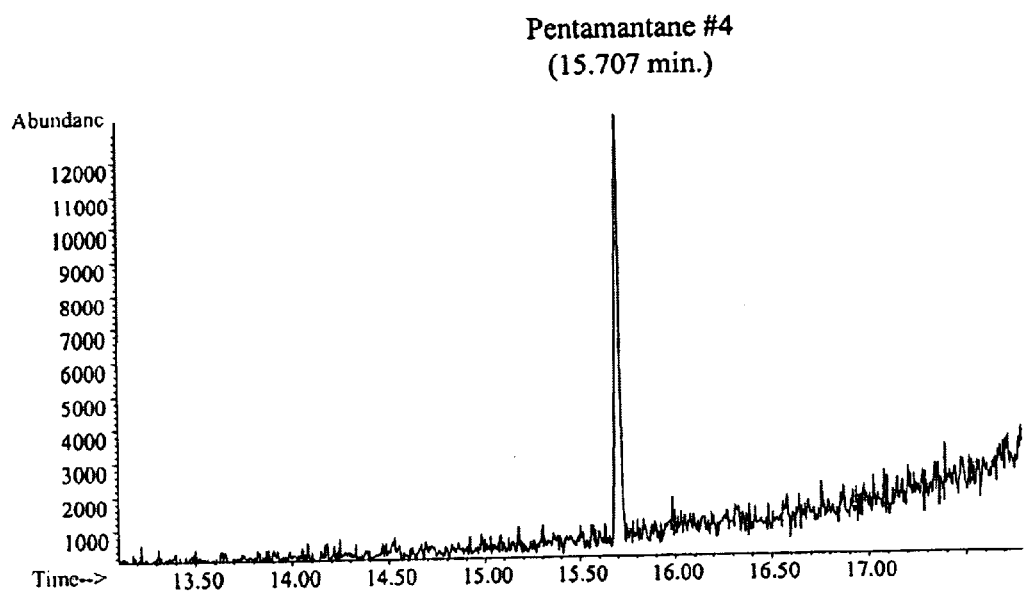
B.
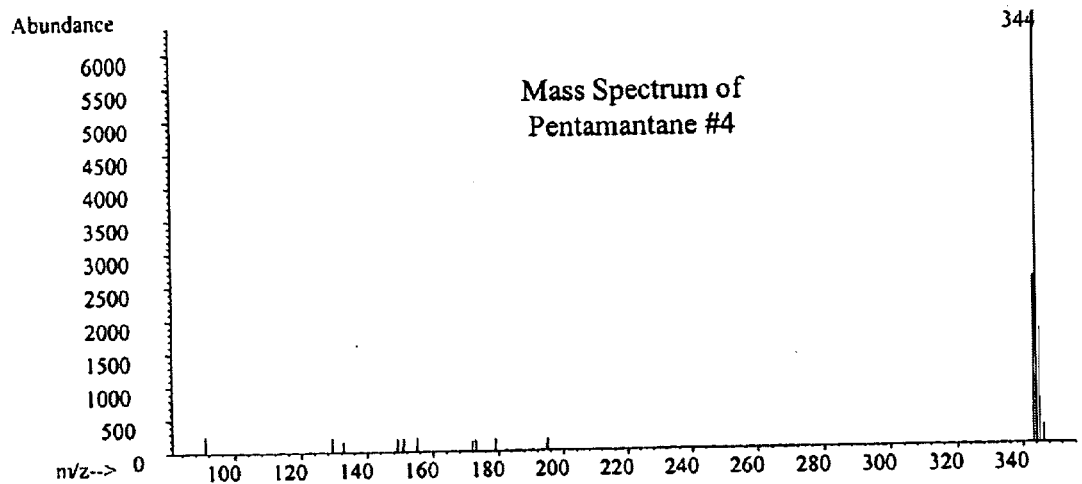

FIG. 20
A.
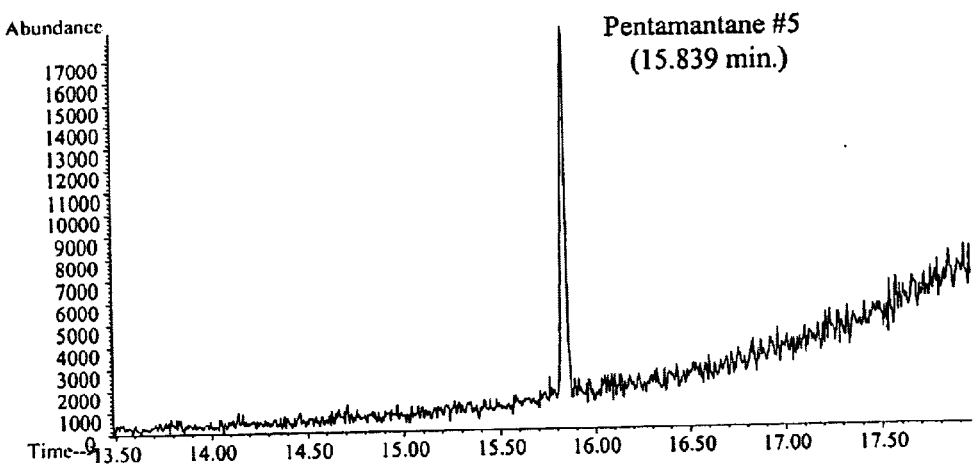
B.
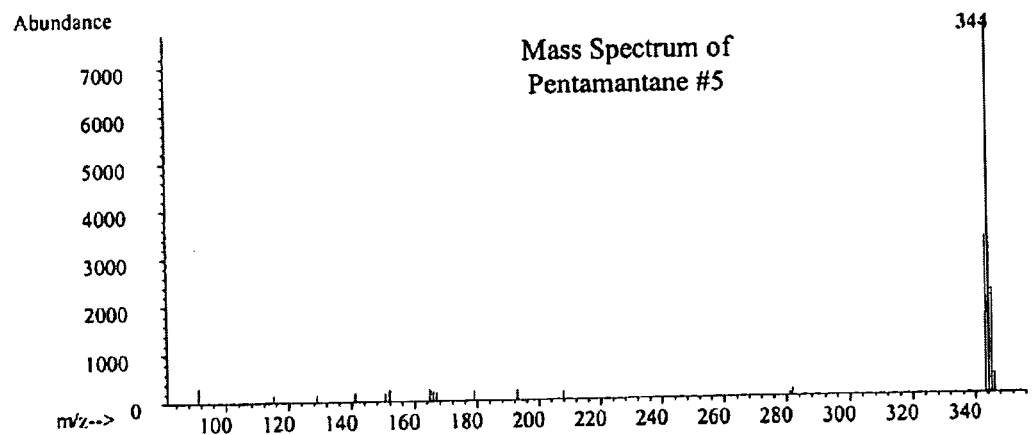

FIG. 21
A.
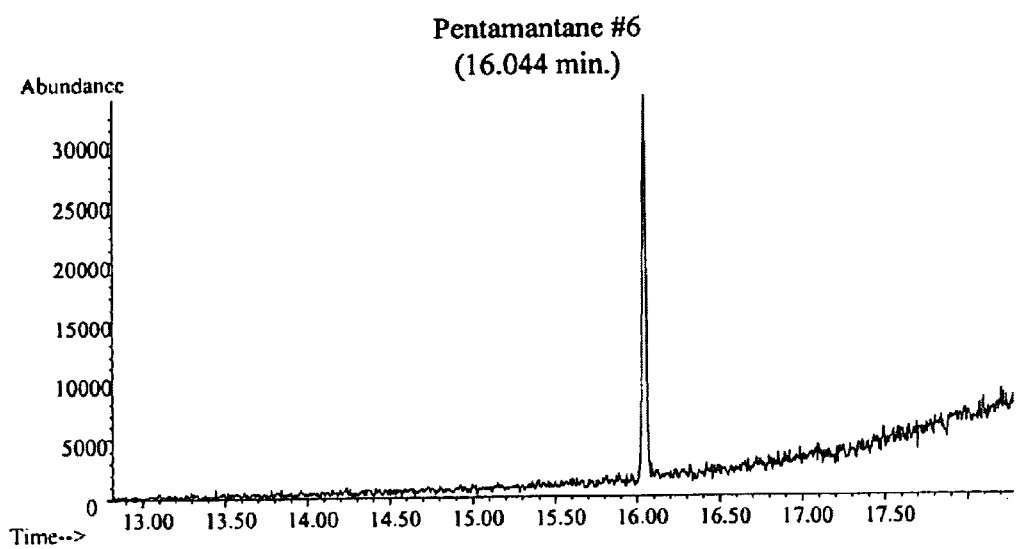
B.
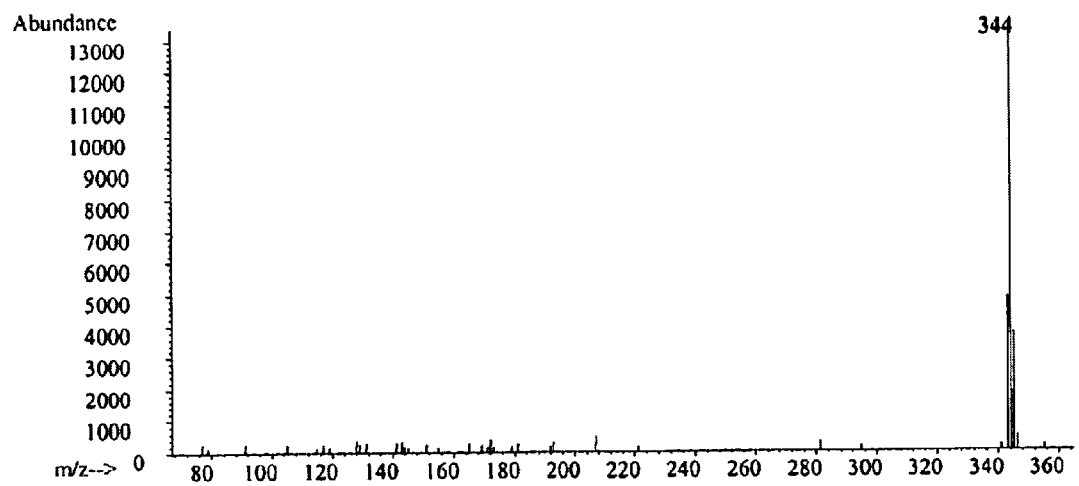

FIG. 22 Pentamantane – Enantiomer A
$C_{26}H_{32}$, $C_1$ Symmetry
Molecular Weight = 344.542
Exact Molecular Weight = 344.2504012
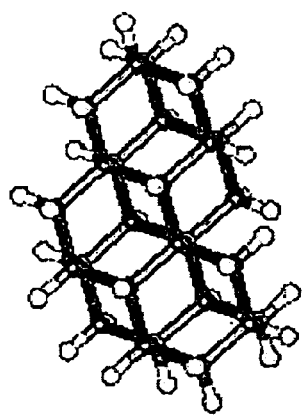
Ball and Stick Representation
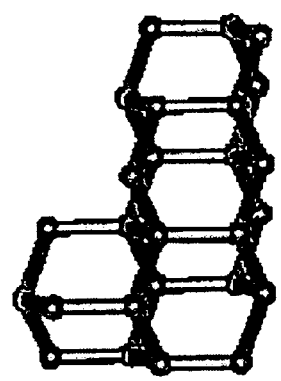
Carbon Framework
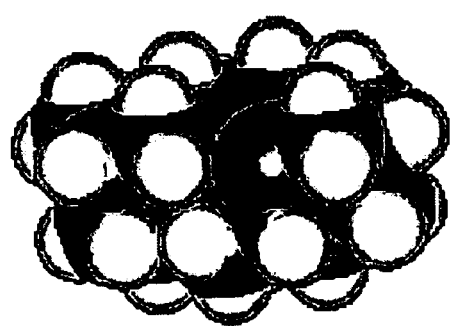
CPK Representation

[1213] Pentamantane – Enantiomer A
View into Specified Diamond Crystal Lattice Plane

111　　　　　110　　　　　100

FIG. 24 Pentamantane – Enantiomer B
$C_{26}H_{32}$, $C_1$ Symmetry
Molecular Weight = 344.542
Exact Molecular Weight = 344.2504012
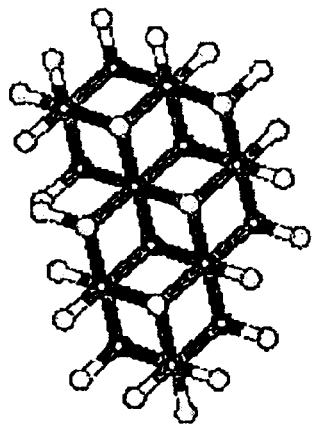
Ball and Stick Representation
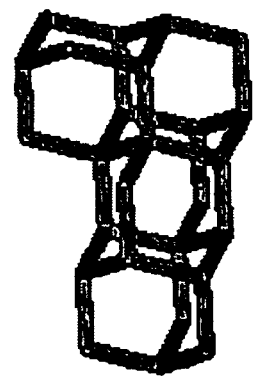
Carbon Framework
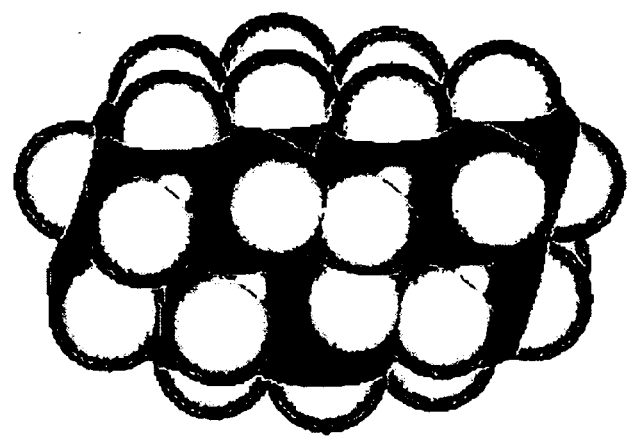
CPK Representation

[1213] Pentamantane – Enantiomer B
View into Specified Diamond Crystal Lattice Plane

| 111 | 110 | 100 |

FIG. 26 Pentamantane – Enantiomer A
$C_{26}H_{32}$, $C_2$ Symmetry
Molecular Weight = 344.542
Exact Molecular Weight = 344.2504012
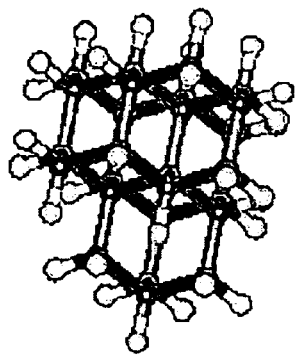
Ball and Stick Representation
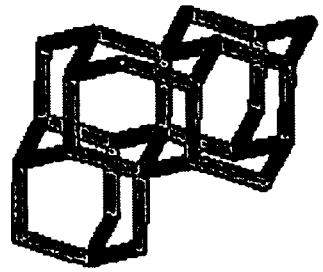
Carbon Framework
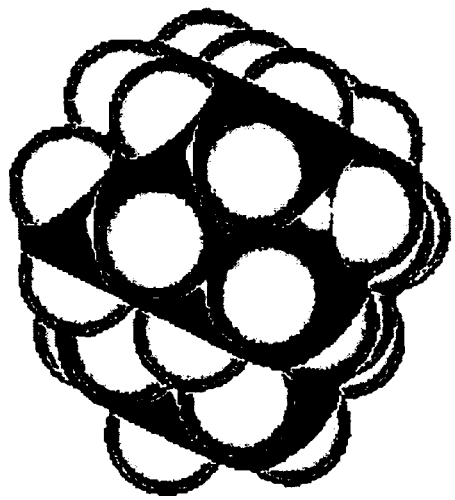
CPK Representation

[1234] Pentamantane – Enantiomer A
View into Specified Diamond Crystal Lattice Plane

FIG. 28 Pentamantane – Enantiomer B
$C_{26}H_{32}$, $C_2$ Symmetry
Molecular Weight = 344.542
Exact Molecular Weight = 344.2504012
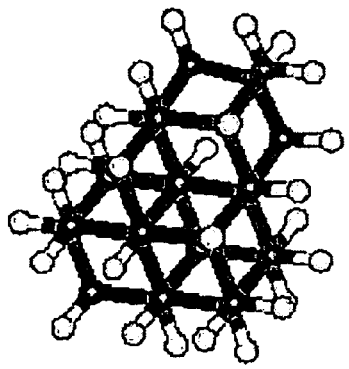
Ball and Stick Representation
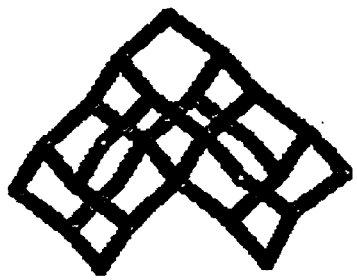
Carbon Framework
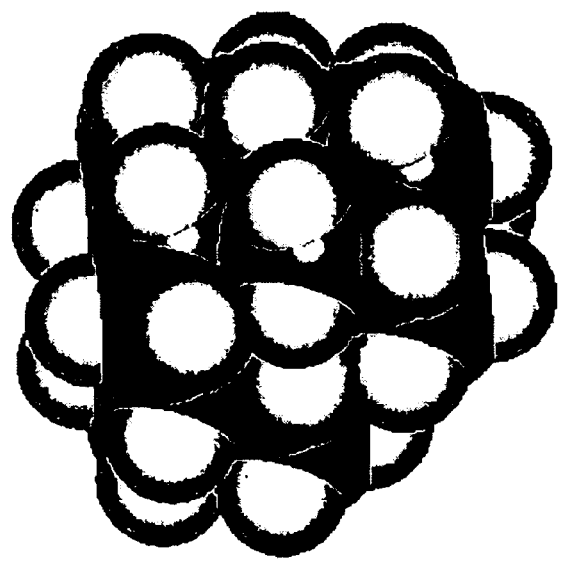
CPK Representation

FIG. 29 Pentamantane – Enantiomer B
View into Specified Diamond Crystal Lattice Plane
| 111 | 110 | 100 |
|---|---|---|
| 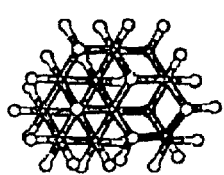 | 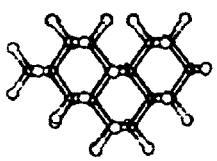 | 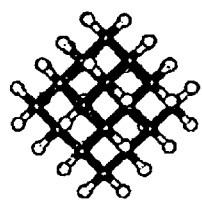 |
| 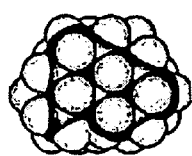 | 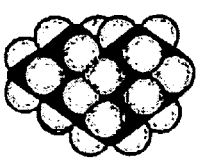 | 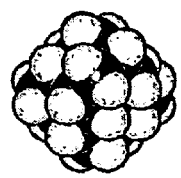 |
| 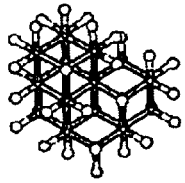 | 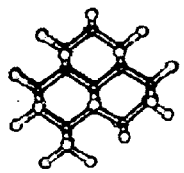 | 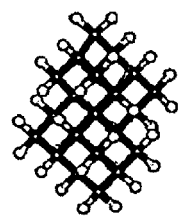 |
| 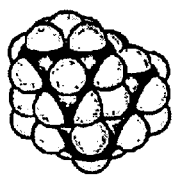 | 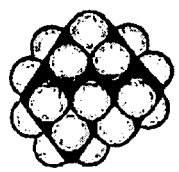 | 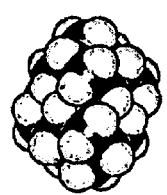 |
| 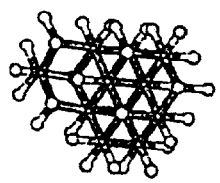 | 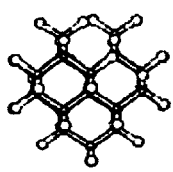 | 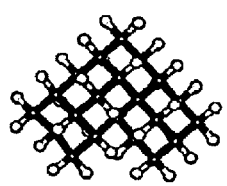 |
| 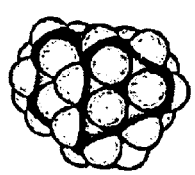 | 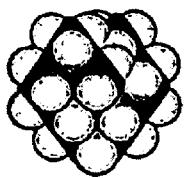 | 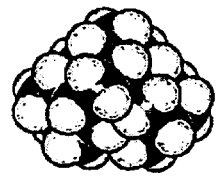 |

FIG. 30
[12(1)3] Pentamantane – Enantiomer A
$C_{26}H_{32}$, $C_1$ Symmetry
Molecular Weight = 344.542
Exact Molecular Weight = 344.2504012
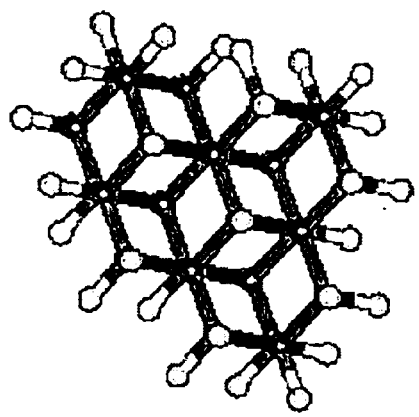
Ball and Stick
Representation
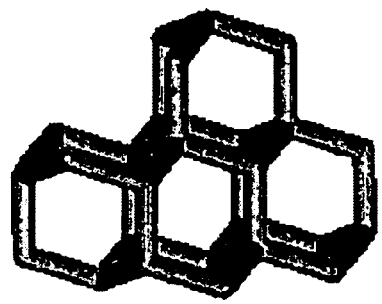
Carbon
Framework
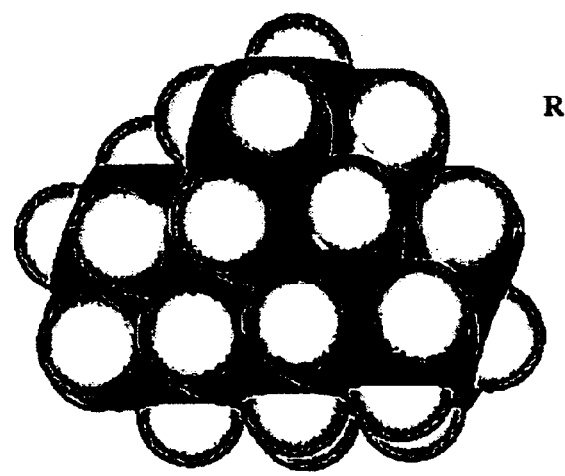
CPK
Representation

FIG. 31
[12(1)3] Pentamantane - Enantiomer A
View into Specified Diamond Crystal Lattice Plane
111    110    100
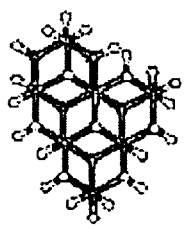
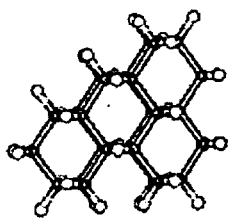
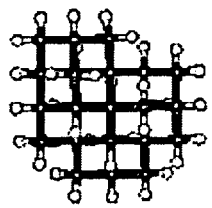
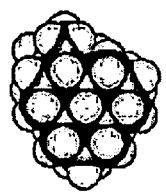
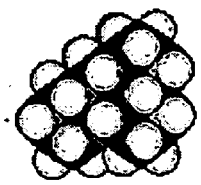
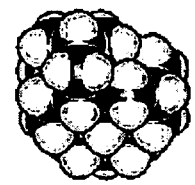
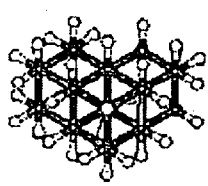
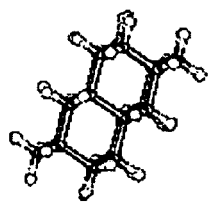
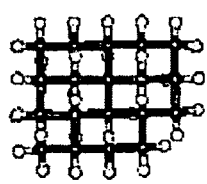
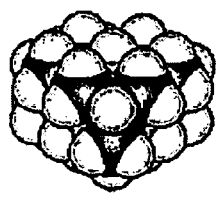
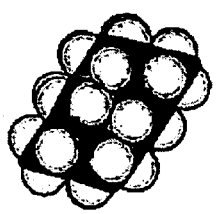
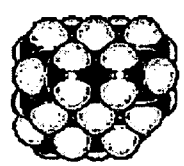
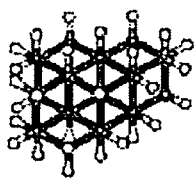
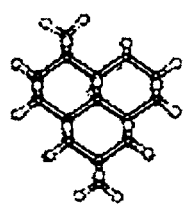
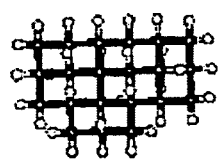
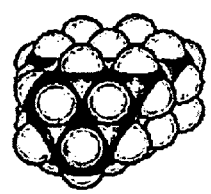
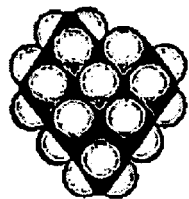
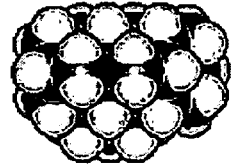

FIG. 32
[12(1)3] Pentamantane - Enantiomer B
$C_{26}H_{32}$, $C_1$ Symmetry
Molecular Weight = 344.542
Exact Molecular Weight = 344.2504012
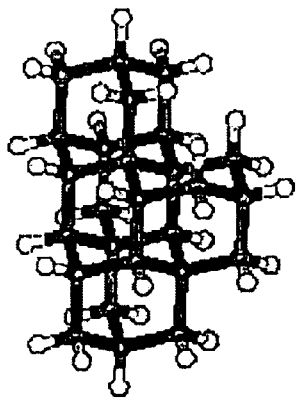
Ball and Stick Representation
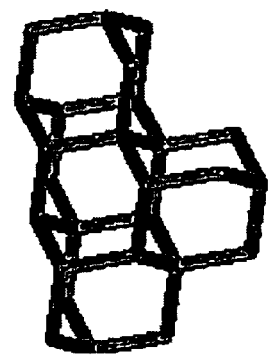
Carbon Framework
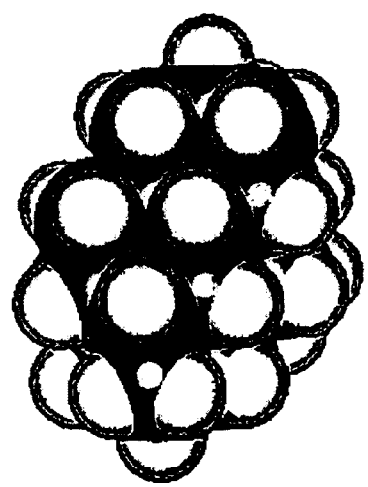
CPK Representation

FIG. 33
[12(1)3] Pentamantane – Enantiomer B
View into Specified Diamond Crystal Lattice Plane
| 111 | 110 | 100 |
|---|---|---|
| 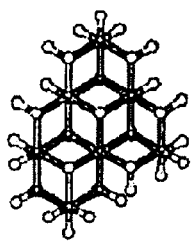 | 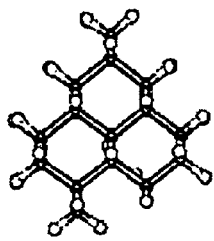 | 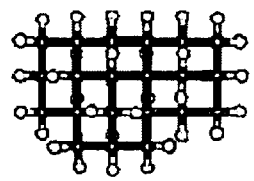 |
| 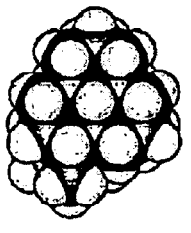 | 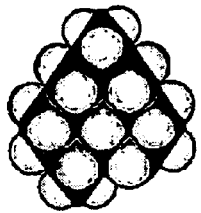 | 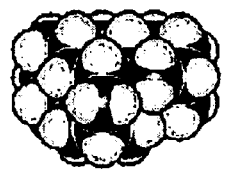 |
| 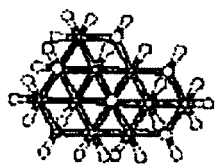 | 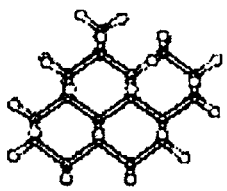 | 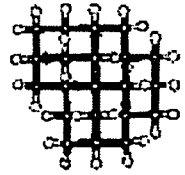 |
| 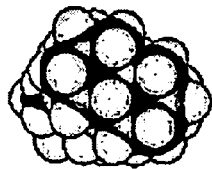 | 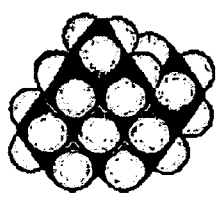 | 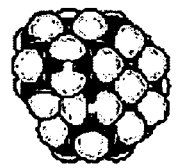 |
| 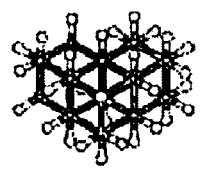 | 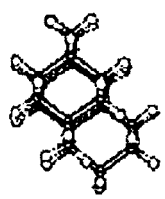 | 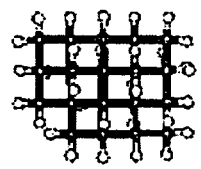 |
| 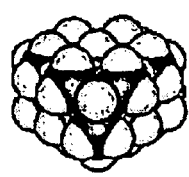 | 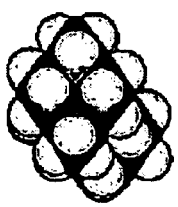 | 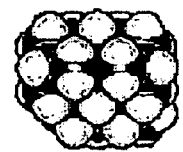 |

FIG. 34 Pentamantane
$C_{26}H_{32}$, $C_{2v}$ Symmetry
Molecular Weight = 344.542
Exact Molecular Weight = 344.2504012
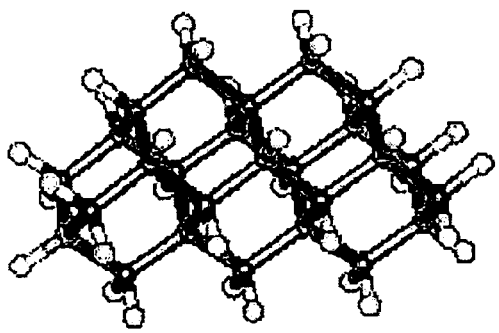
Ball and Stick Representation
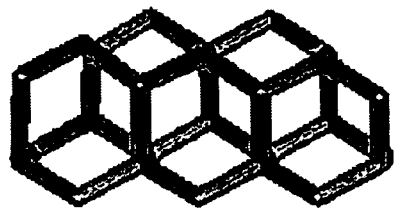
Carbon Framework
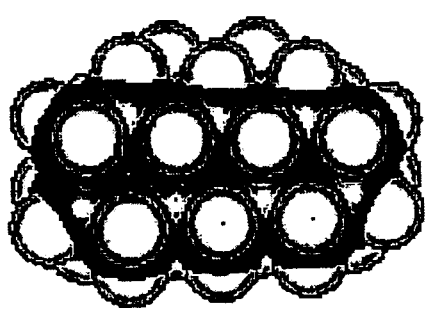
CPK Representation

[1212] Pentamantane
View into Specified Diamond Crystal Lattice Plane 111      110      100

[1(2,3)4] Pentamantane
Neopentamantane
$C_{26}H_{32}$, Td Symmetry
Molecular Weight = 344.542
Exact Molecular Weight = 344.2504012

FIG. 37
[1(2,3)4] Pentamantane
View into Specified Diamond Crystal Lattice Plane
| 111 | 110 | 100 |
|---|---|---|
| 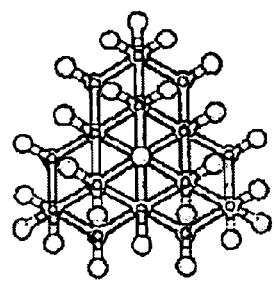 | 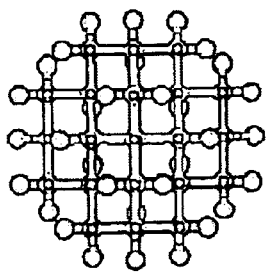 | 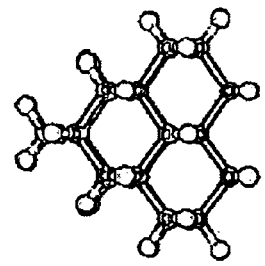 |
| 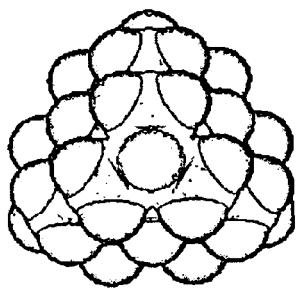 | 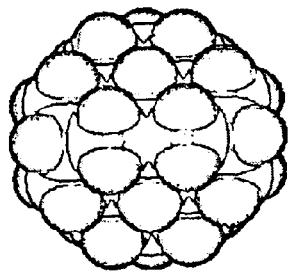 | 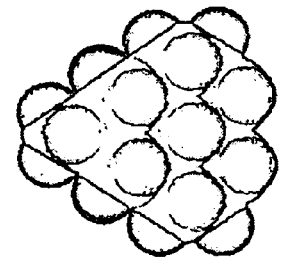 |
| 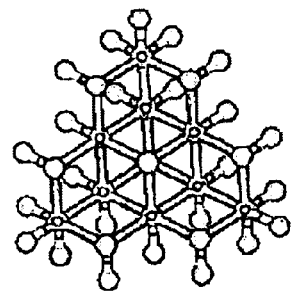 | 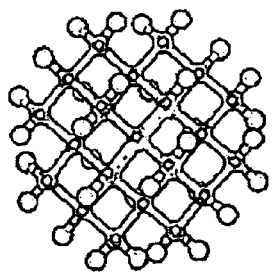 | 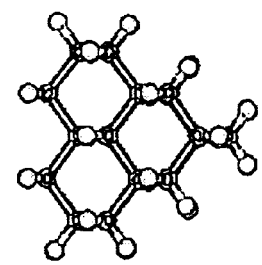 |
| 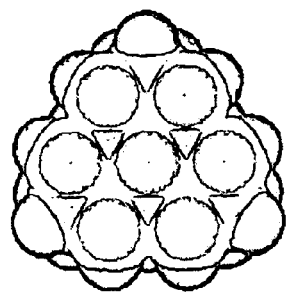 | 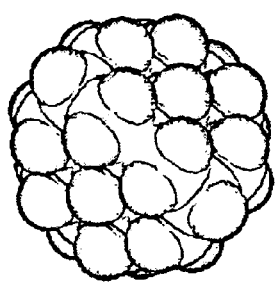 | 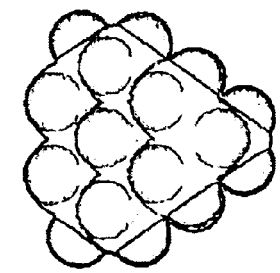 |

FIG. 38 Pentamantane
$C_{25}H_{30}$, $C_s$ Symmetry
Molecular Weight = 30.515
Exact Molecular Weight = 330.2347511
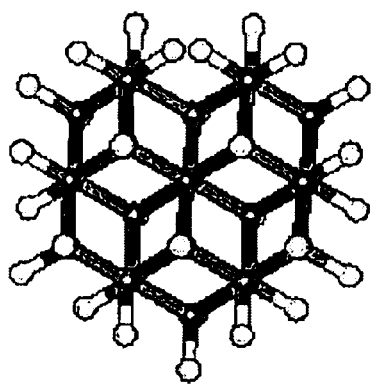
Ball and Stick
Representation
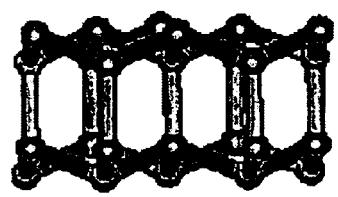
Carbon
Framework
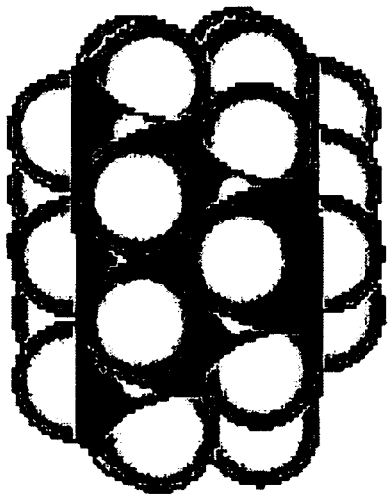
CPK
Representation

[1231] Pentamantane
View into Specified Diamond Crystal Lattice Plane 111      110      100

FIG. 40
[12(3)4] Pentamantane
$C_{26}H_{32}$, $C_S$ Symmetry
Molecular Weight = 344.542
Exact Molecular Weight = 344.2504012
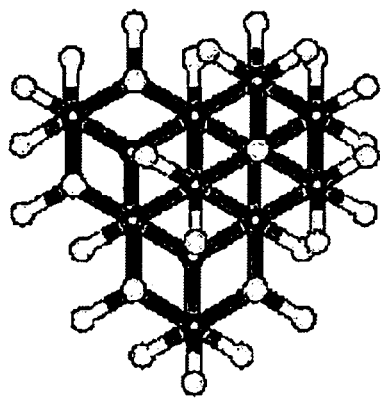
Ball and Stick
Representation
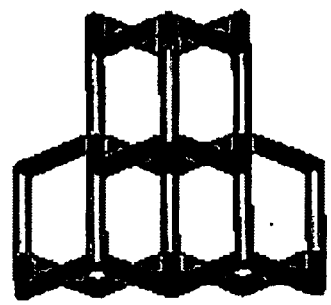
Carbon
Framework
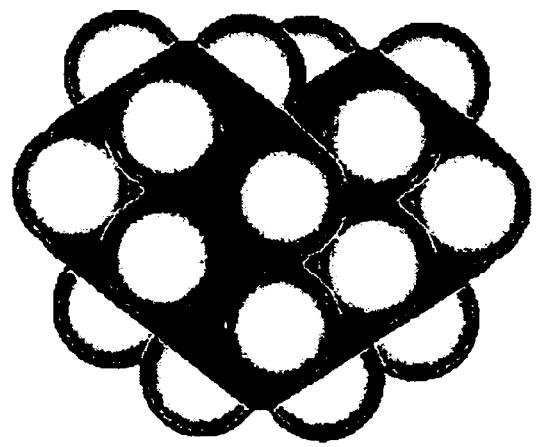
CPK
Representation

[12(3)4] Pentamantane
View into Specified Diamond Crystal Lattice Plane

FIG. 42
TIC: 0104031.D
Total Ion Chromatogram
ODS HPLC 18
Fr. 31
A.
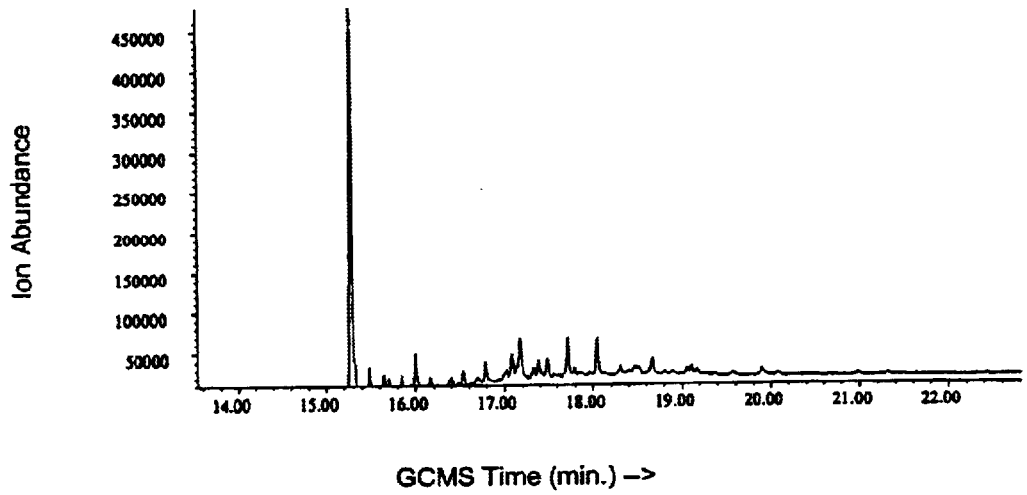
B.
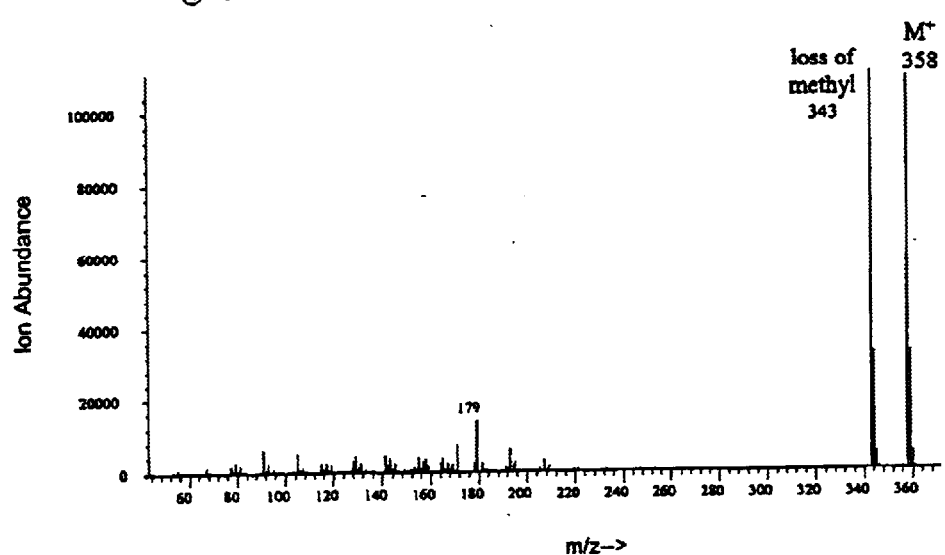

COMPOSITIONS COMPRISING PENTAMANTANES AND PROCESSES FOR THEIR SEPARATION

REFERENCE TO RELATED APPLICATIONS

This application claims priority under 35 USC 1.119(e) to U.S. Provisional Application Ser. No. 60/262,842 filed Jan. 19, 2001 and to U.S. Provisional Application Ser. No. 60/307,063 filed Jul. 20, 2001, both of which are incorporated by reference.

BACKGROUND OF THE INVENTION

1. Field of the Invention

This invention is directed to novel compositions comprising one or more pentamantanes. This invention is also directed to novel processes for the separation and isolation of pentamantane components into recoverable fractions from a feedstock containing one or more pentamantane components.

2. References

The following publications and patents are cited in this application as superscript numbers:

[1] Lin, et al., *Natural Occurrence of Tetramantane ($C_{22}H_{28}$), Pentamantane ($C_{26}H_{32}$) and Hexamantane ($C_{30}H_{36}$) in a Deep Petroleum Reservoir*, Fuel, 74(10):1512–1521 (1995)

[2] Alexander, et al., Purification of Hydrocarbonaceous Fractions, U.S. Pat. No. 4,952,748, issued Aug. 28, 1990

[3] McKervey, *Synthetic Approaches to Large Diamondoid Hydrocarbons*, Tetrahedron, 36:971–992 (1980).

[4] Wu, et al., High Viscosity Index Lubricant Fluid, U.S. Pat. No. 5,306,851, issued Apr. 26, 1994.

[5] Chung et al., *Recent Development in High-Energy Density Liquid Fuels*, Energy and Fuels, 13; 641–649 (1999).

[6] Sandia National Laboratories (2000), *World's First Diamond Micromachines Created at Sandia*, Press Release, (Feb. 22, 2000) www.Sandia.gov.

[7] Balaban et al., *Systematic Classification and Nomenclature of Diamondoid Hydrocarbons-I*, Tetrahedron. 34, 3599–3606 (1978).

[8] Chen, et al., Isolation of High Purity Diamondoid Fractions and Components, U.S. Pat. No. 5,414,189 issued May 9, 1995.

All of the above publications and patents are herein incorporated by reference in their entirety to the same extent as if each individual publication or patent was specifically and individually indicated to be incorporated by reference in its entirety.

3. State of the Art

Pentamantanes are bridged-ring cycloalkanes. They are the face-fused pentamers of adamantane (tricyclo[3.3.1.1$^{3,7}$] decane) or $C_{10}H_{16}$. The compounds have a "diamondoid" topology, which means their carbon atom arrangement is superimposable on a fragment of the diamond lattice (FIG. 1). There are ten possible pentamantanes (FIG. 2). Nine of the ten have the molecular formula $C_{26}H_{32}$. Among these nine, there are three pairs (six pentamantanes) that are enantiomers. In addition, there exists one condensed pentamantane represented by the formula $C_{25}H_{30}$.

Very little published work is available for pentamantanes and higher molecular weight diamondoids. Pentamantane compounds have not been artificially synthesized and these compounds have been recently thought only to have a theoretical existence.[1,7] Academic chemists have primarily focused research on the interplay between physical and chemical properties in lower diamondoids such as adamantane, diamantane and triamantane. Adamantane and diamantane, for instance, have been studied to elucidate structure-activity relationships in carbocations and radicals.[3] Process engineers have directed efforts toward removing lower diamondoids from hydrocarbon gas streams.[2] These compounds cause problems during the production of natural gas by solidifying in pipes and other pieces of equipment.

The literature contains little information regarding the practical application of pentamantanes. This fact is probably due to extreme difficulties with their isolation and failed synthesis attempts. Lin and Wilk, for example, discuss the possible presence of pentamantanes in a gas condensate.[1] The researchers postulate the existence of the compounds based on a mass spectrometric fragmentation pattern. They did not, however, report the isolation of a single pentamantane. McKervey et al. discuss an extremely low-yielding synthesis of anti-tetramantane.[3] The procedure involves complex starting materials and employs drastic reaction conditions (e.g., gas phase on platinum at 360° C.). Although one isomer of tetramantane, i.e. anti-, has been synthesized through a double homologation route, these syntheses are quite complex reactions with large organic molecules in the gas phase and have not led to the successful synthesis of other tetramantanes. Similar attempts using preferred-ring starting materials in accordance with the homologation route, has likewise failed in the synthesis of pentamantanes. Likewise, attempts using carbocation rearrangement routes employing Lewis acid catalysts, useful in synthesizing triamantane and lower diamondoids, have been unsuccessful in synthesizing pentamantanes.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$) and excellent thermal conductivity.

In addition, based on theoretical considerations, the pentamantanes have sizes in the nanometer range and, in view of the properties noted above, the inventors contemplate that such compounds would have utility in micro- and molecular-electronics and nanotechnology applications. In particular, the rigidity, strength, stability, thermal conductivity, variety of structural forms and multiple attachment sites shown by these molecules makes possible accurate construction of robust, durable, precision devices with nanometer dimensions. The various pentamantanes are three-dimensional nanometer-sized units showing different diamond lattice arrangements. This translates into a variety of rigid shapes and sizes for the ten pentamantanes. For example, [1212] pentamantane is rod shaped, [1(2,3)4] pentamantane has a pyramidal structure while [1231] is disc shaped. The two enantiomers of [1234] have left and right handed screw-like structures. It has been estimated that MicroElectroMechanical Systems (MEMs) constructed out of diamond should last 10,000 times longer than current polysilicon MEMs, and diamond is chemically benign and would not promote allergic reactions in biomedical applications.[6] Again, the inventors contemplate that pentamantane would have similar attractive properties. Furthermore, some of the isomers of pentamantane possess chirality, offering opportunities for making nanotechnology objects of great structural specificity with useful optical properties. Applications of these pentamantanes include molecular electronics, photonic devices, nanomechanical devices, nanostructured polymers and other materials.

Notwithstanding these advantages of pentamantanes, the art, as noted above, fails to provide for compositions comprising pentamantanes. In view of the above, there is an ongoing need in the art to provide for compositions comprising one or more pentamantanes.

SUMMARY OF THE INVENTION

This invention is directed to novel compositions comprising one or more pentamantane components.

Accordingly, in one of its composition aspects, this invention is directed to a composition comprising one or more pentamantane components wherein said composition comprises at least about 25 weight percent pentamantane components based on the total weight of the diamondoids in the composition.

In another of its composition aspects, the compositions preferably comprise one or more pentamantane components wherein the pentamantane components make up from about 50 to 100 weight percent, preferably about 70 to 100 weight percent, more preferably about 90 to 100 weight percent and even more preferably about 95 to 100 weight percent of the total weight of the diamondoids in the compositions.

In another of its composition aspects, the compositions comprise at least about 10 weight percent and preferably at least about 20 weight percent of pentamantanes based on the total weight of the composition. Other compositions of this invention contain from 50 to 100 weight percent, 70 to 100 weight percent, 95 to 100 weight percent and 99 to 100 weight percent of pentamantanes based on the total weight of the composition.

In another of its composition aspects, the compositions preferably comprise from about 70 to 100 weight percent, more preferably from about 90 to 100 weight percent, even more preferably from about 95 to 100 weight percent and most preferably from about 99 to 100 weight percent of a single pentamantane component, including isolated optical isomers thereof, based on the total weight of the composition.

In an additional aspect, this invention is directed to isolated pentamantane components characterized by the base structures of [1213] A and B, [1234] A and B, [12(1)3] A and B, [1212], [1(2,3)4], [1231] and [12(3)4] and mixtures thereof. When pentamantane components are of a high purity, such pentamantane components can form crystals. Thus, this invention is directed to crystals of a pentamantane component or of a mixture of two or more pentamantane components.

This invention is also directed to novel processes for the separation and isolation of pentamantane components into recoverable fractions from a feedstock containing one or more pentamantane components and nonpentamantane materials. These processes for recovering a composition enriched in pentamantane components entail removing at least a portion of the nonpentamantane materials which have a boiling point below the lowest boiling pentamantane component and utilizing a subsequent separation technique to recover pentamantane components from the resulting residue. Accordingly, this aspect is directed to processes which comprise:

a) selecting a feedstock comprising recoverable amounts of pentamantane components and nonpentamantane materials;

b) removing from the feedstock a sufficient amount of nonpentamantane materials that have boiling points below the boiling point of the lowest boiling point pentamantane component in the feedstock under conditions to form a treated feedstock enriched in pentamantane components which can be recovered;

c) recovering pentamantane components by separating said treated feedstock formed in b) above with one or more additional separation techniques selected from the group consisting of chromatographic techniques, thermal diffusion techniques, zone refining, progressive recrystallization and size separation techniques.

In a preferred embodiment, after the step recited in b) the treated feedstock can be thermally treated to pyrolyze at least a sufficient amount of nondiamondoid components therefrom under conditions to provide a thermally treated feedstock retaining recoverable amounts of pentamantane. Such a pyrolization step prior to step c) is useful for thermally degrading at least a portion of any materials remaining in the treated feedstock having a thermal stability lower than the pentamantane components. This pyrolysis step can be carried out before step b) if desired.

BRIEF DESCRIPTION OF THE DRAWINGS

FIG. 1 illustrates the correlation of the structures of diamondoids to subunits of the diamond crystal lattice.

FIG. 3 illustrates the gas chromatogram of a gas condensate feedstock; one of the original feedstocks used in the Examples (Feedstock A). Pentamantanes are present at low concentrations, not detectable, but are shown in vacuum distillation fractions (FIG. 6)

FIG. 4 illustrates a simulated distillation profile of a gas condensate feedstock containing petroleum byproducts used in the Examples (Feedstock B). Boiling points depicted are atmospheric equivalents. Pentamantanes were found in the atmospheric residue (650° F.+) of Feedstock B.

FIGS. 7(A, B) illustrates the preparative capillary gas chromatographic data for pentamantane isolations.

FIG. 7A, shows the first column cut containing one of the pentamantanes from thermally treated Feedstock B. The material in that cut was separated on a second column.

FIG. 7B, shows the second column peak sent to the trap. Pentamantane #1, the first pentamantane to elute in GC/MS analysis, was isolated in the trap.

FIGS. 8(A,B) shows the GC/MS total ion chromatogram and mass spectrum of pentamantane #1 isolated by preparative capillary gas chromatography.

FIG. 9(A) is a photomicrograph of pentamantane #1 crystals isolated from Feedstock B by preparative gas chromatography (FIG. 7 and 8).

FIG. 9B illustrates a pentamantane co-crystal.

FIGS. 11(A, B, C) illustrates the gas chromatograms of vacuum distillate Fractions #3, #4, and #5 of Feedstock B atmospheric distillation 650° F.+bottoms illustrated in FIG. 10 and exemplified in Example 1.

FIGS. 12(A,B) illustrates the concentration of pentamantanes using pyrolysis.

FIG. 12A is the GC of Feedstock B distillation fraction #5, exemplified in Example 1, which was used as feedstock in pyrolytic processing.

FIG. 12B is the GC of the product of the pyrolytic process.

FIG. 14 illustrates the preparative HPLC data of Feedstock B distillation cut pyrolysis product saturated hydrocarbon fraction showing HPLC fractions taken using a Hypercarb column and acetone mobile phase. Each pentamantane component shows a different elution time on this HPLC system as indicated on the chart. Pentamantane components are numbered in order of their elution on the GC/MS analyses. The "x" marks the fractions containing the highest concentration of individual pentamantanes.

FIGS. 16(A, B) illustrates GCIMS total ion chromatogram (TIC) and mass spectrum of pentamantane component #1 isolated using two different HPLC columns.

FIGS. 17(A, B) illustrates GCIMS total ion chromatogram (TIC) and mass spectrum of pentamantane component #2 isolated using two different HPLC columns.

FIGS. 18(A, B) illustrates GC/MS total ion chromatogram (TIC) and mass spectrum of pentamantane component #3 isolated using two different HPLC columns.

FIGS. 19(A, B) illustrates GC/MS total ion chromatogram (TIC) and mass spectrum of pentamantane component #4 isolated using two different HPLC columns.

FIGS. 20(A, B) illustrates GC/MS total ion chromatogram (TIC) and mass spectrum of pentamantane component #5 isolated using two different HPLC columns.

FIGS. 21(A, B) illustrates GC/MS total ion chromatogram (TIC) and mass spectrum of pentamantane component #6 isolated using two different HPLC columns.

FIGS. 22 through 41 illustrate the structures with views into various diamond crystal lattice planes for each of the ten pentamantane components.

FIGS. 42(A,B) illustrates GC/MS total ion chromatogram (TIC) and mass spectrum of a methylpentamantane (mol. wt 358) purified by ODS HPLC.

DETAILED DESCRIPTION OF THE INVENTION

This invention is directed to compositions comprising one or more pentamantane components. However, prior to describing this invention in further detail, the following terms will first be defined.

Definitions

As used herein, the following terms have the following meanings.

Figure 1:
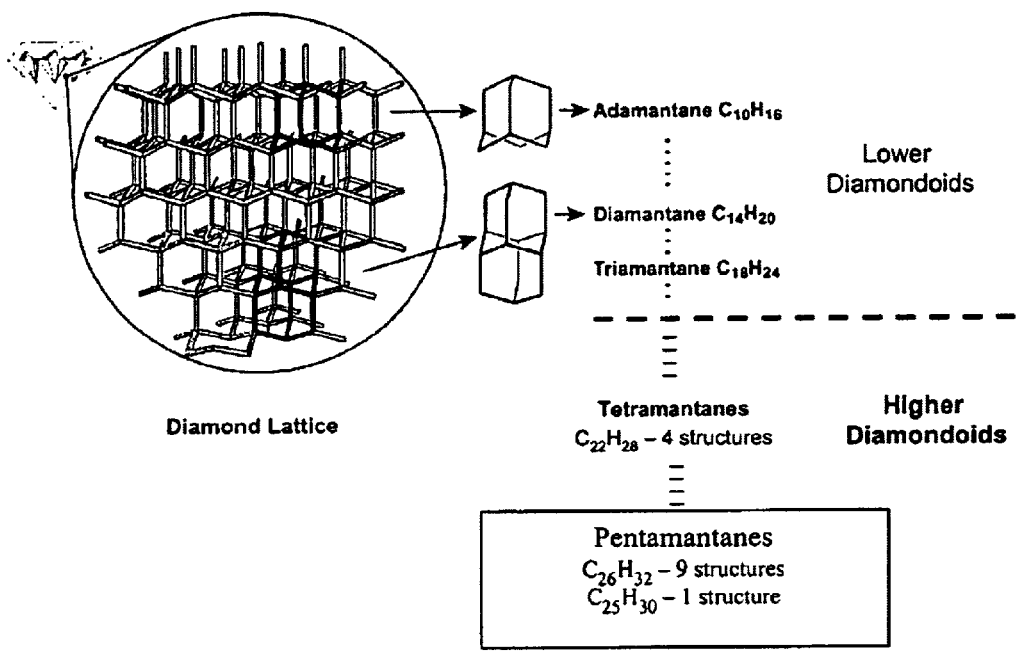
FIG. 1 illustrates the cage-shaped structure of diamondoids and their correlation to diamonds. Specifically.
Figure 2:
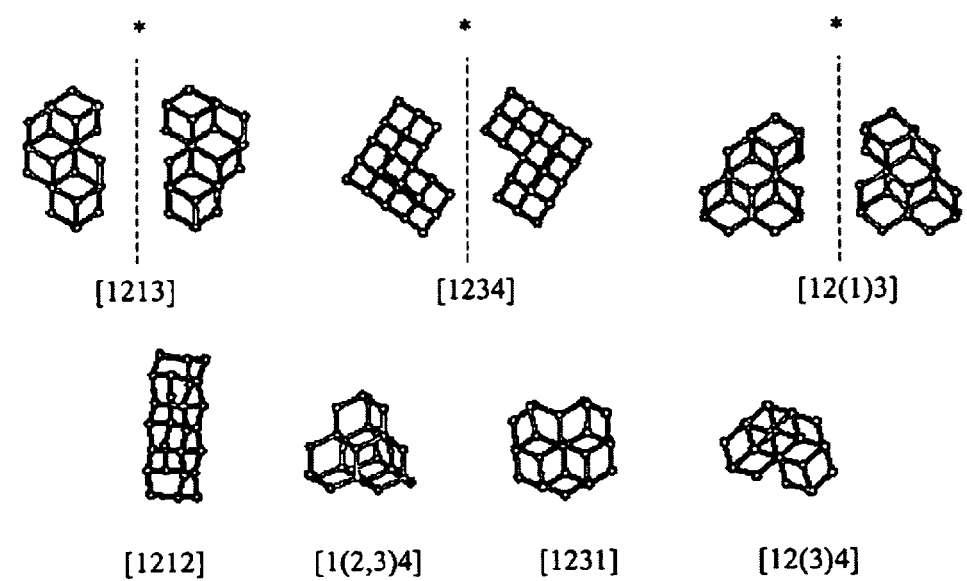
FIG. 2 illustrates the structure of the 10 pentamantane isomers of which there are three enantiomeric pairs.

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like and also including all isomers and stereoisomers thereof. The compounds have a "diamondoid" topology, which means their carbon atom arrangement is superimposable on a fragment of the diamond lattice (FIG. 1). Substituted diamondoids comprise from 1 to 10 and preferably 1 to 4 independently-selected alkyl substituents. Diamondoids include "lower diamondoids," "pentamantanes," "higher diamondoids" and "nonpentamantane higher diamondoids" as these terms are defined herein.

The term "pentamantanes" refers to diamondoids that are the face-fused pentamers of adamantane. There are ten possible unsubstituted pentamantanes. Nine of the ten have the molecular formula ($C_{26}H_{32}$). Among these nine, there are three pairs (six pentamantanes) that are enantiomers. In addition, there exists one nonisomeric condensed unsubstituted pentamantane represented by the formula $C_{25}H_{30}$. Each of the pentamantane isomers possesses a different three-dimensional structure. "Pentamantanes" include "substituted" materials as described for diamondoids, generally.

The term "pentamantane component" refers to any single substituted or unsubstituted pentamantane, including optical isonomers (enantiomers).

The term "lower diamondoids" or "adamantane, diamantane and triamantane components" refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids".

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, and undecamantane. Those higher diamondoids which are not pentamantane components are referred to as "nonpentamantane higher diamondoids."

The term "feedstock" or "hydrocarbonaceous feedstock" refers to hydrocarbonaceous materials comprising recoverable amounts of one or more pentamantane components. Preferably, such feedstocks include gas condensates, refinery streams, and oil including oil derived from reservoir rocks, oil shale, tar sands, source rocks, and the like. Such feedstocks typically, but not necessarily, comprise lower diamondoids and other higher diamondoids as well as non-diamondoid components. Nondiamondoid components include materials boiling below and above the unsubstituted pentamantanes which exhibit atmospheric equivalent boiling points of about 370° to about 450° C. Typical feedstocks may also contain impurities such as sediment, metals including nickel and vanadium and other inorganics. They may also contain heteromolecules containing sulfur, nitrogen and the like. All of these materials which are not pentamantane components are referred to as "nonpentamantane materials" or "nonpentamantane components".

The term "enriched" when used to describe the state of purity of one or more pentamantane components refers to such materials at least partially separated from nonpentamantane materials, and in the case of "enriched" individual pentamantane components, from other pentamantane components so as to be at a concentration at least 25 and preferably at least 100 times as great as the concentration exhibited in a feedstock. Preferably "enriched" pentamantane or "enriched" pentamantane components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%–95% or 99% of such material.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" and "distilling" refer to atmospheric, reduced pressure distillation, and elevated pressure distillation conducted to concentrate pentamantane components by removal of nonpentamantane components from the feedstock based on boiling points. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal degradation" and "pyrolytic processing" and the like refer to processes for treating a feedstock or a feedstock fraction at elevated temperature to selectivity break down and/or pyrolyze at least a portion of nondiamondoid components in the feedstock or feedstock fraction.

The term "nondiamondoid components" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The enriched pentamantanes of this invention can be obtained from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures. Detailed descriptions of methods for processing feedstocks to enrich and isolate higher diamond compositions are set forth in U.S. Provisional Patent Application No. 60/262,842 filed Jan. 19, 2001 and U.S. Provisional Patent Application No. 60/300,148 filed Jun. 21, 2001. These applications are herein incorporated by reference in their entirety.

To obtain the pentamantane compositions described herein, a feedstock is selected such that said feedstock comprises recoverable amounts of pentamantane. Preferably, such feedstock comprises at least about 1 ppb of pentamantane components. It is understood, of course, that feedstocks having higher concentrations of pentamantanes facilitate recovery of these materials.

Preferred feedstocks include, for example, natural gas condensates and refinery streams having high concentrations of higher diamondoids. With regard to the latter, such refinery streams include hydrocarbonaceous streams recoverable from cracking processes, distillations, coking and the like. Particularly preferred feedstocks include natural gas condensates from the Norphlet Formation in the Gulf of Mexico and from the LeDuc Formation in Canada.

The feedstocks used to obtain the compositions of this invention typically comprise nondiamondoid components having boiling points both below and above the pentamantane components as well as lower diamondoids and nonpentamantane higher diamondoids. A sufficient amount of these contaminants is removed from the feedstocks to provide treated feedstocks from which the pentamantane components can be enriched and recovered.

The removal of nondiamondoids, lower diamondoids and nonpentamantane higher diamondoids can be carried out, by way of example only, using size separation techniques such as membranes, molecular sieves, etc., evaporation and thermal separators either under normal or reduced pressures, extractors, crystallization, chromatography, well head separators, and the like. A preferred separation method typically includes distillation of the feedstock to remove nondiamondoid components as well as nonpentamantane diamondoids having boiling points less than that of the lowest boiling point pentamantane component. Temperature profiles for distillation runs and the resulting distillation cuts can be determined on the basis of the pentamantane component of interest. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In each instance, the lower cuts, which are enriched in lower diamondoids and low boiling point nondiamondoid components, are discarded. Distillation can be operated to provide several cuts in the temperature range of interest to provide the initial isolation of the identified pentamantane. The cuts, which are enriched in pentamantane or a particular pentamantane component of interest, are retained and may require further purification. For recovery of pentamantanes, the preferred distillation cuts are taken at atmosphere equivalent boiling point temperatures of from 330° to about 490° C., preferably from 360° to about 450° C., especially 385° to 425° C. Additional temperature refinements will allow for higher purity cuts for the pentamantane of interest. Other methods for the removal of contaminants and further purification of an enriched pentamantane fraction can additionally include the following nonlimiting examples: size separation techniques, evaporation either under normal or reduced pressure, crystallization, chromatography, well head separators, reduced pressure and the like.

The contaminant removal may also include a thermal degradation step either prior to or subsequent to distillation. Thermal degradation is an effective method to remove hydrocarbonaceous, nondiamondoid components from the feedstock. It is effected by heating the feedstock under vacuum conditions or in an inert atmosphere, at a temperature of at least about 390° C. or 400° C. (preferably about 410° C. to about 475° C., most preferably about 410° C. to about 450° C. for from 5 to 30 hours). The specific conditions employed are selected such that recoverable amounts of pentamantane components are retained in the feedstock. The selection of such conditions is well within the skill of the art. Preferably, thermal degradation is continued for a sufficient period of time and at a sufficiently high enough temperature to thermally degrade at least about 10% by weight of the nondiamondoids components of the feed material prior to thermal degradation. More preferably at least 50% and even more preferably at least 90% of the nondiamondoids are thermally degraded.

Thermal degradation, while a preferred embodiment, is not always necessary to facilitate the recovery, isolation or purification of the pentamantane components. Other separation methods may allow for the concentration of these pentamantane components to be sufficiently high in certain feedstocks that direct purification methods such as chromatography including preparative gas chromatography and high performance liquid chromatography and crystallization may be used to isolate pentamantane components.

Even after distillation or thermal degradation/distillation, further purification of the pentamantane components may be desired to provide the compositions of this invention. One may use purification techniques such as chromatography, crystallization, thermal diffusion techniques, zone refining, progressive recrystallization, size separation and the like. For instance, the treated feedstock can be subjected to one or more of the following additional procedures: 1) gravity column chromatography using silver nitrate impregnated silica gel; 2) multicolumn preparative capillary gas chromatography; 3) single column high performance liquid chromatography; 4) high performance liquid chromatography with multiple columns of differing selectivity; and 5) crystallization to provide crystals of the highly concentrated pentamantanes. These provisions can be combined. For example, preparative capillary gas chromatography can be coupled with high performance liquid chromatography as a first or subsequent separation method.

Further processing using these methods allow for more refined separations which can lead to a pure pentamantane component. Enantioselective (chiral) stationary phases could be applied in chromatographic methods to effectuate further separations. High performance liquid chromatography methods also offer the possibility of using chiral solvents or additives to achieve resolution of enantiomers.

For example, separation of enantiomeric forms of the pentamantanes can be achieved using several approaches. One such approach is spontaneous crystallization with resolution and mechanical separation. This approach to enantiomer resolution can be enhanced by preparation of derivatives or by the use of additives, chiral solvents, or various types of seed crystals.

Another resolution option is chemical separation under kinetic or thermodynamic control. Other suitable processes for enantiomers resolution include chiral separations, which can be preformed using a gas chromatographic (GC) see "Chiral Chromatography", T. E. Beesley, et. al, Wiley, Johnson & Sons, January 1998, incorporated herein by reference, by high performance liquid chromatographic (HPLC) and by supercritical fluid chromatographic (SFC) techniques, see "Supercritical fluids in Chromatography and Extraction", R. M. Smith, Elsevier Science, December 1997, incorporated herein by reference.

Compositions

This invention is directed to compositions comprising one or more pentamantane components wherein said compositions comprise at least about 25 weight percent pentamantane components based on the total weight of the diamondoids in the compositions. The compositions preferably comprise from about 50 to 100 weight percent, preferably about 70 to about 100 weight percent, more preferably about 90 to 100 weight percent and even more preferably about 95 to 100 weight percent pentamantane components based on the total weight of the diamondoids in the composition.

Such pentamantane-enriched compositions are obtained through the series of unit operations described above which can be used to concentrate pentamantanes to at least 25 times and more preferably at least 100 times the levels at which they occur in readily-available feedstocks. The total weight percent of pentamantane components in the compositions is preferably at least 10% by weight based upon the total weight of the composition. In a more preferred aspect the total weight percent of pentamantane components is from 50 to 100 weight percent, more preferably 70 to 100 weight percent and even more preferably 95 or 99 to 100 weight percent based upon the total weight percent of the composition.

In other aspects, the compositions comprise an enriched individual pentamantane component such that they contain from 70 to 100 weight percent, more preferably from 90 to 100 weight percent, even more preferably from 95 to 100 weight percent and most preferably from 99 to 100 weight percent of a single pentamantane component including isolated optical isomers thereof.

Figure 39:
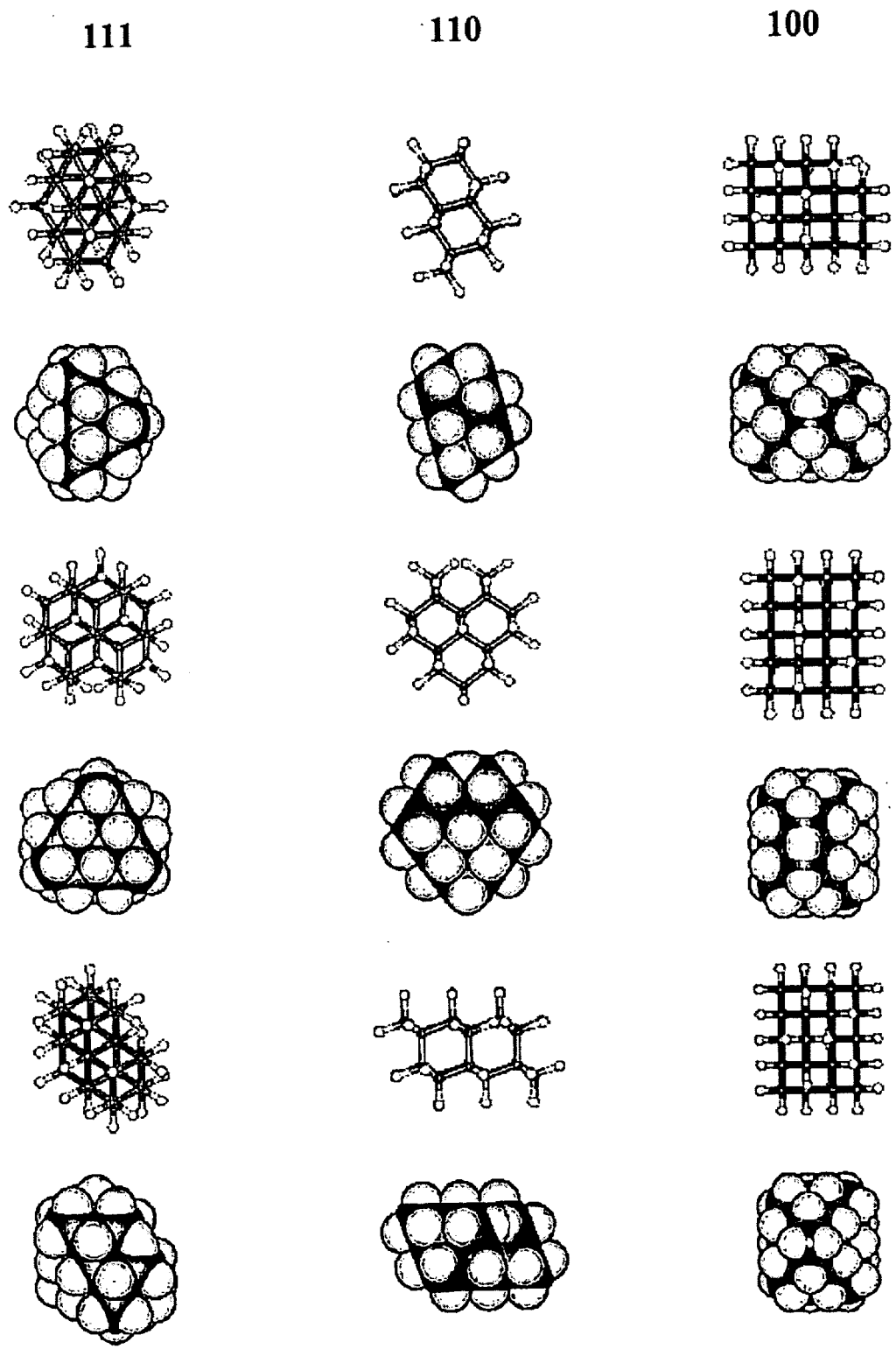
Figure 41:
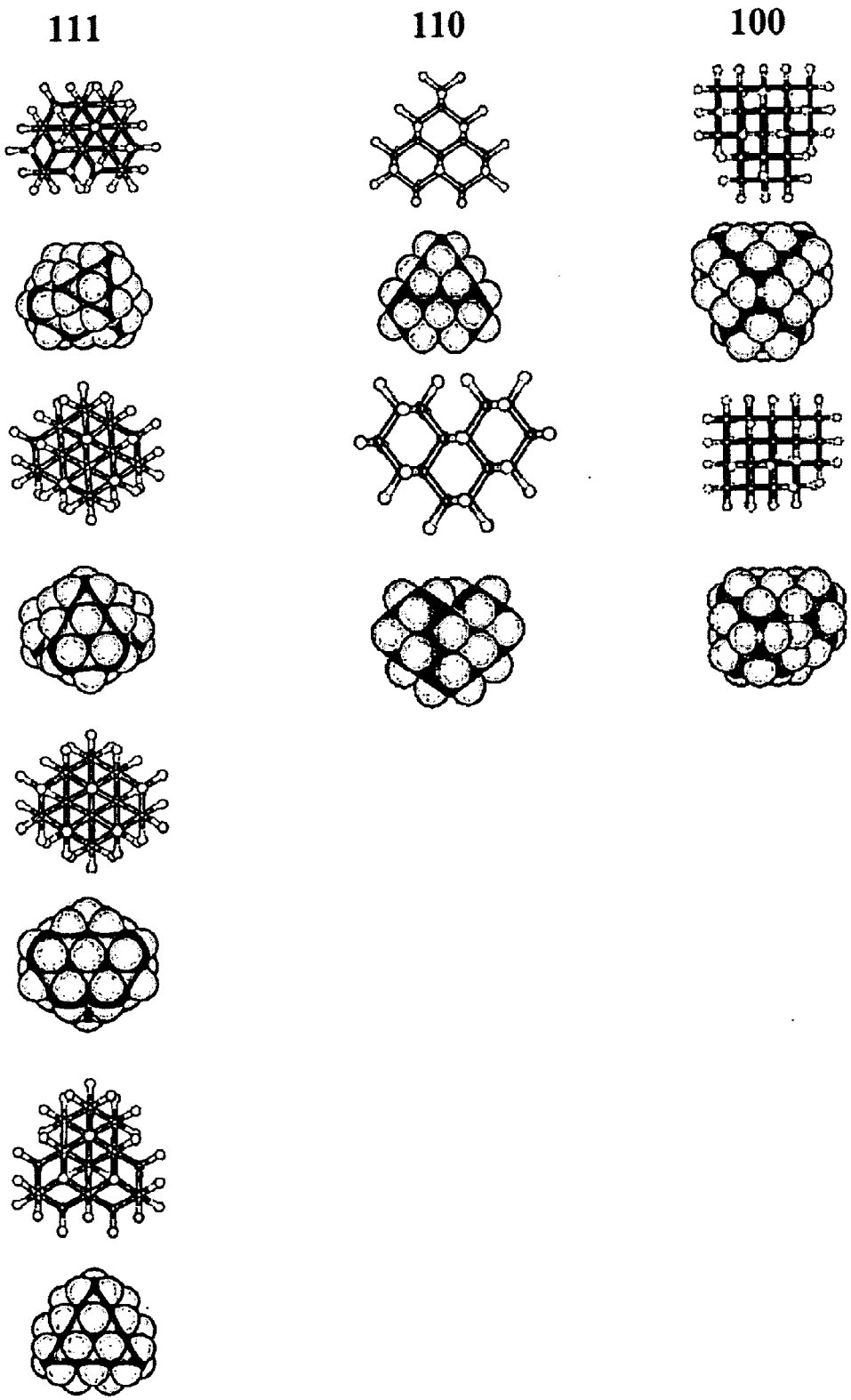

There are ten unsubstituted pentamantane components. This invention provides methodology for isolating each of them for the first time. There is a single pentamantane component represented by the molecular formula $C_{25}H_{30}$ (molecular weight 330) with the structure and diamond lattice planes represented by FIGS. 38–39. This component is named "[1231] pentamantane" using the convention outlined in Balaban et al[7]. This material is sterically stressed and appears in lower concentrations than the remaining pentamantanes. The remaining nine pentamantanes have the molecular formula $C_{26}H_{32}$ (molecular weight 344). They occur in higher concentration than the 330 molecular weight pentamantane. Views into various diamond crystal lattice planes for pentamantanes are shown in FIGS. 22–37 and 40–41. The individual pentamantane components are named:

[1213] enantiomer A pentamantane;
[1213] enantiomer B pentamantane;
[1234] enantiomer A pentamantane;
[1234] enantiomer B pentamantane;
[12(1)3] enantiomer A pentamantane;
[12(1)3] enantiomer B pentamantane;

[1212] pentamantane;
[1(2,3)4] pentamantane; and
[12(3)4] pentamantane.

This invention is also directed to mixtures of these ten pentamantane components, as well as substituted pentamantane components alone or together with nonsubstituted materials.

At the high pentamantane concentrations and purities achieved by the present invention, pentamantane components can form crystals. Accordingly, another aspect of this invention is directed to pentamantane crystals, whether crystals of a single pentamantane component, co-crystals comprising crystals of at least two pentamantane components or co-crystals of pentamantane components with other higher diamondoids, such as tetramantane components.

The pentamantanes recovered and isolated in this invention include substituted pentamantane components. These naturally-occurring substituted pentamantanes have similar properties to the unsubstituted pentamantane components described herein and are present in the feedstocks. Substituted pentamantanes may act as useful intermediates in various pentamantane applications or can be de-alkylated to yield the corresponding unsubstituted pentamantanes. Substituted pentamantanes contain 1 to 10 alkyl substituents, and more preferably 1 to 4 such substituents.

The most prevalent substituted pentamantanes in the feedstocks used are pentamantanes substituted with lower alkyls. The most prevalent of these are methyl and ethyl-substituted pentamantanes, including methyl, ethyl, dimethyl, and trimethyl pentamantanes.

Utility

These pentamantane-containing compositions are useful in micro- and molecular-electronics and nanotechnology applications. In particular, the rigidity, strength, stability, thermal conductivity, variety of structural forms and multiple attachment sites shown by pentamantanes makes possible accurate construction of robust, durable, precision devices with nanometer dimensions. These special structural characteristics set these compounds apart from acyclic molecules, from condensed-ring systems and even from bridged-ring counterparts. The great stability, nanometer size, variable yet rigid geometry, well defined distances for places of attachment, nonplanar bridgeheads lead to their unique features. Due to the rigidity, specialized geometry, 3-dimensional shape nanometer size and, in the case of enantiomer pairs; chirality of the pentamantane components, it is expected that molecular aggregates and building blocks comprising them will enable construction and synthesis of a unprecedented array of desirable materials that will find applications in molecular electronic computing devices, reduced-size machines such as molecular robots and self-replicating manufacturing systems. Alternatively, the pentamantanes may be used as novel materials of construction with special chemical, optical, electric and thermal conductivity properties for coatings, film layering and other applications taking advantage of the diamond-like properties, etc.

In addition, pentamantane-containing compositions can also be used in a high-quality lubricant which exhibits a high Viscosity Index and a very low pour point.[4] When so employed, these lubricants comprise from about 0.1 to 10 weight percent pentamantanes.

Still further, these pentamantane-containing compositions can be used as high density fuels in the manner described by Chung, et al.[5], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| | |
|---|---|
| API = | American Petroleum Institute |
| ATM EQV = | atmospheric equivalent |
| EOR Traps = | end of run traps |
| FID = | flame ionization detector |
| G = | grams |
| GC = | gas chromatography |
| GC/MS = | gas chromatography/mass spectroscopy |
| HPLC = | high performance liquid chromatography |
| HYD RDG = | hydrometer reading |
| MIN = | minute |
| ML = | milliliters |
| ODS = | octadecylsilane |
| pA = | pico amps |
| ppb = | parts per billion |
| RI = | refractive index |
| SFC = | super critical fluid chromatography |
| SIM DIS = | simulated distillation |
| ST = | start |
| TIC = | total ion current |
| VLT = | vapor line temperature |
| VOL PCT = | volume percent |
| WT PCT = | weight percent |

EXAMPLES

Example 1

Isolation of Pentamantane Components

The purpose of this example is to demonstrate procedures for the isolation of pentamantane components. These procedures employed Feedstock B and a pyrolysis step, however this procedure could be facilitated using other materials, such as Feedstock A, and without the pyrolysis step. After removal of lower boiling point nonpentamantane components (including some lower diamondoids and tetramantanes from the feedstock by distillation), the pentamantane components in this example were recovered by chromatography and crystallization. The distillation preferably can be operated to provide specific cuts, thus removing both lower and higher boiling point components, leaving only components within a desired boiling point range.

Step 1

Suitable starting materials were obtained. These materials included a gas condensate, Feedstock A (a gas chromatogram of this material is depicted in FIG. 3), and a gas condensate containing petroleum byproducts Feedstock B (a high temperature simulated distillation profile of this type of material is depicted in FIG. 4). Although other condensates, petroleums, or refinery cuts and products could have been used, these two materials were chosen due to their high concentration of higher diamondoids (0.3 weight percent), as determined by GC and GC/MS. Both feedstocks were light colored and had API gravities between 19 and 20° API.

Step 2

Samples from Feedstocks A and B were distilled into a number of fractions based on boiling points to separate the lower boiling point components (nondiamondoids and lower diamondoids) and to further concentrate and enrich pentamantanes in various fractions. The yields of atmospheric distillate fractions of two separate samples of Feedstock B are shown in Table 1, below and are contrasted to the simulated distillation yields calculated for that feedstock. As seen from Table 1, the simulation data are in agreement with the distillation data.

TABLE 1

Yields of Atmospheric Distillation Fractions
from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | -0.7 |
| 491 to 643 | 31.0 | 30.6 | 0.4 |
| 643 and higher | 4.0 | 4.1 | -0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | -2.5 |
| 515 to 649 | 28.5 | 31.2 | -2.7 |
| 649 and higher | 3.5 | 2.1 | 1.4 |

Figure 5:
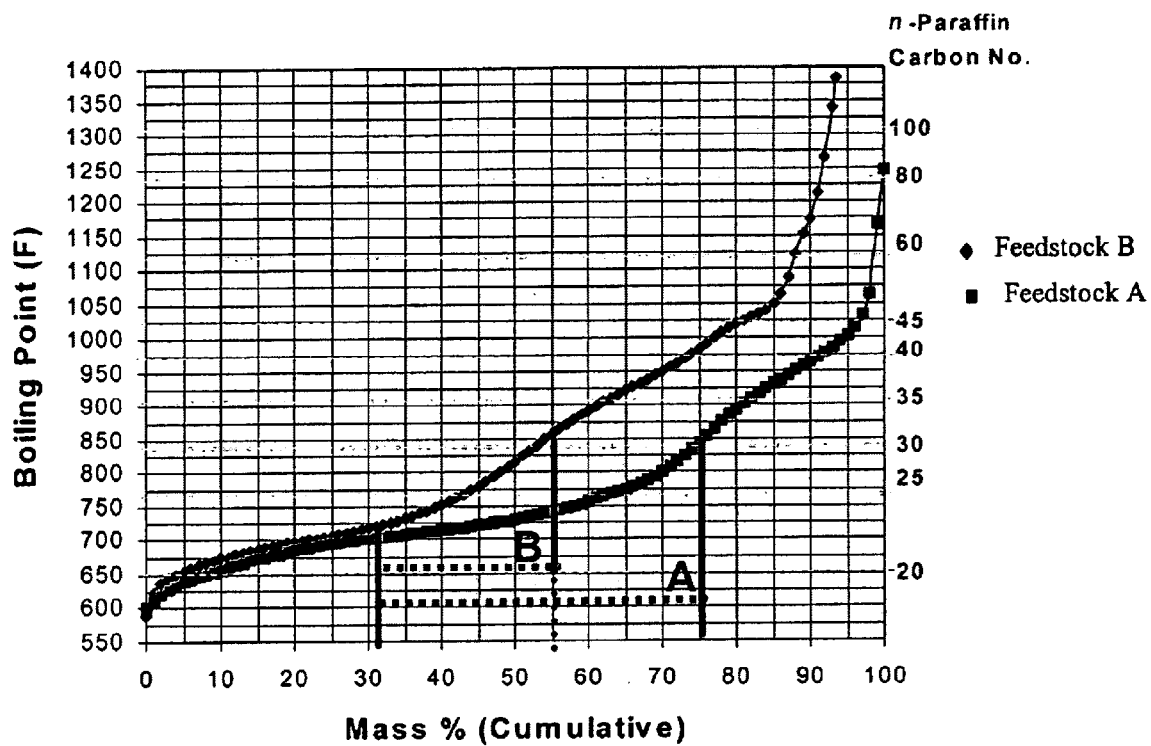
FIG. 5 illustrates a high temperature simulated distillation profile of atmospheric residue of diamondoid rich gas condensates; Feedstock A and Feedstock B. This Figure also illustrates the n-paraffin carbon number atmospheric equivalent boiling points. Labels A and B show the portions of each feedstock which contain the pentamantanes.

The higher diamondoid-containing atmospheric residue fraction from Feedstock B was in the 2 to 4 weight percent range as shown in Table 1. FIG. 5 compares a high-temperature simulated distillation profile of the atmospheric residue of the gas condensates, Feedstock A and Feedstock B. Additionally outlined is the identified location and size of the pentamantane-containing fractions. In terms of atmospheric equivalent boiling points the pentamantanes were anticipated to be predominately within the range of 330 to about 490° C. with a large portion within the range of 385 to about 425° C. The lower mass percent shown for the pentamantane-containing fractions of Feedstock B, as compared to Feedstock A was due to nondiamondoid materials in Feedstock B. The nondiamondoid material can be removed by subsequent processes such as pyrolysis.

A sample of gas condensate, Feedstock A was distilled into 38 fractions to remove lower diamondoids and concentrate higher diamondoids including pentamantanes as verified by GC (see FIG. 6) wherein residue left after distillation of Fraction 38 was recovered, predominately boiling in the range of from 700 to 850° F. (atmospheric equivalent). The boiling points of these fractions are given as atmospheric equivalent temperatures, however, the actual distillation can occur at other pressures and corresponding temperatures.

Figure 6:
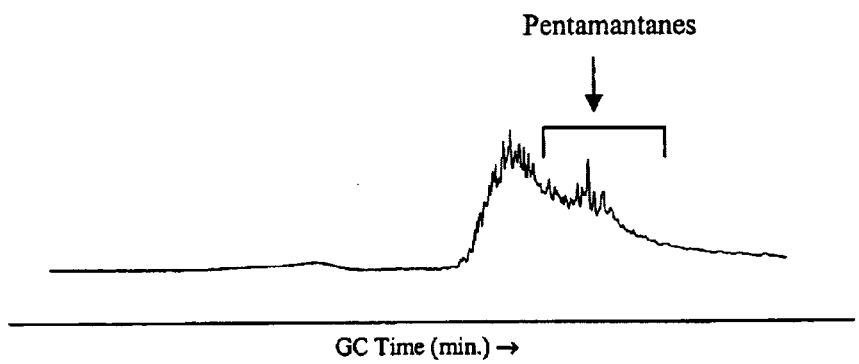
FIG. 6 illustrates a gas chromatographic profile of a distillate residue containing pentamantanes and higher diamondoids from a gas condensate, Feedstock A.
Figure 10:
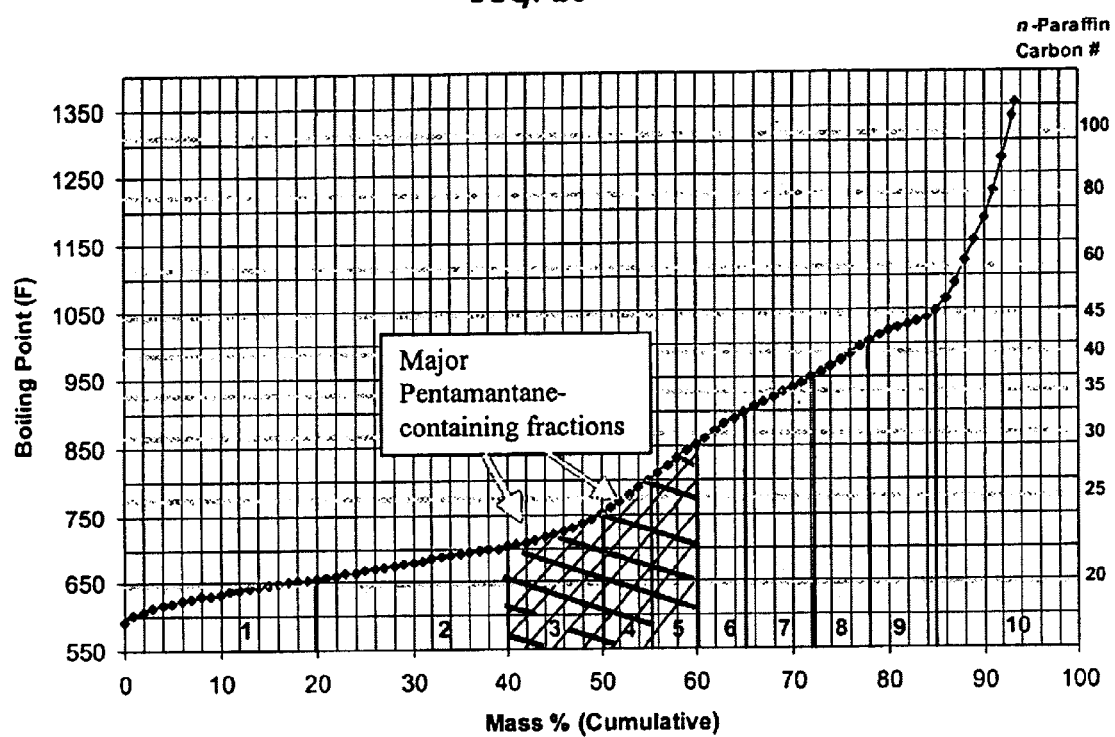
FIG. 10 illustrates a high temperature simulated distillation profile of Feedstock B using the atmospheric distillation 650° F.+bottoms as feedstock. This FIG. also illustrates the targeted cut points (1-10) for diamondoid isolations. Pentamantanes are contained primarily in distillate fractions 3 through 5. Boiling points are atmospheric equivalents.

Additionally, Feedstock B was distilled into fractions containing higher diamondoids guided by a high-temperature simulated-distillation curve (FIG. 10). The primary pentamantane-containing Fractions (3–5) are marked on FIG. 10. FIG. 11 shows a GC analysis trace for distillate fractions corresponding to Fractions 3, 4 and 5 in FIG. 10. Comparison of FIGS. 6 and 11 shows that Feedstock B contained impurities not present in Feedstock A. The feed to the high temperature distillation process was the atmospheric 650° F. +bottoms. Complete Feedstock B distillation reports are given in Tables 2A&B. Tables 3A&B, illustrate the distillation reports for Feedstock B 643° F. +distillation bottoms.

TABLE 2A

Distillation Report for Feedstock B
(FSL #8471)
Feedstock B
Column Used: Clean 9" x 1.4" Protruded Packed

| | VAPOR | DISTILLATION RECORD | | | | NORMALIZED | | ACTUAL | |
|---|---|---|---|---|---|---|---|---|---|
| CUT | TEMP ° F. ST – END | WEIGHT G | VOLUME ml @ 60° F. | API 60/60 | DENSITY @ 60° F. | WT PCT | VOL PCT | WT PCT | VOL PCT |
| 1 | 226 – 349 | 67.0 | 80 | 38.0 | 0.8348 | 7.61 | 8.54 | 7.39 | 8.26 |
| 2 | 349 – 491 | 507.7 | 554 | 22.8 | 0.9170 | 57.65 | 59.12 | 55.98 | 57.23 |
| 3 | 491 – 643 | 269.6 | 268 | 9.1 | 1.0064 | 30.62 | 28.60 | 29.73 | 27.69 |
| COL HOLDUP | | 0.2 | 0 | 6.6 | 1.0246 | 0.02 | 0.00 | 0.02 | 0.00 |
| BTMS 643 + | | 36.1 | 35 | 6.6 | 1.0246 | 4.09 | 3.74 | 3.98 | 3.62 |
| EOR TRAPS | | 0.0 | 0 | | | 0.00 | 0.00 | | 0.00 |
| TOTALS | | 880.6 | 937 | | | 100.00 | 100.00 | 97.09 | 96.80 |
| LOSS | | 26.4 | 31 | | | | | 2.91 | 3.20 |
| FEED | | 907.0 | 968 | 19.5 | 0.9371 | | | 100.00 | 100.00 |
| BACK CALCULATED API AND DENSITY | | | | 19.1 | 0.9396 | | | | |

TABLE 2B

Distillation Report for Feedstock B
(FSL #8471)
Feedstock B
Column Used: Clean 9" x 1.4" Protruded Packed

| TEMPERATURE DEGREES F. | | | | | | | | | API GRAVITIES | |
|---|---|---|---|---|---|---|---|---|---|---|
| VAPOR | | | | | | | | | OBSERVED | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 93 | 225.8 | 262 | 50.000 | 3:1 | | | | START OVERHEAD | | |

TABLE 2B-continued

Distillation Report for Feedstock B
(FSL #8471)
Feedstock B
Column Used: Clean 9" × 1.4" Protruded Packed

| TEMPERATURE DEGREES F. | | | | | | | | | API GRAVITIES | |
|---|---|---|---|---|---|---|---|---|---|---|
| VAPOR | | | | | | | | | OBSERVED | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| Cut 2 looks Milky, White crystals form in Run Down Line. Heat Lamp applied to drip tube. | | | | | | | | | | |
| Cool to transfer btms to smaller flask. | | | | | | | | | | |
| 208 | 437.7 | 323 | 10.000 | 3:1 | | START OVERHEAD | | | | |
| 378 | 643.3 | 550 | 10.000 | 3:1 | 3 | 268 | 269.6 | 9.9 | 75.0 | 9.1 |
| Shutdown due to dry pot | | | | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B
(FSL #8691)
Feedstock B - Atmospheric distillation resid 650° F. + bottoms
Column Used: Sarnia Hi Vac

| TEMPERATURE DEGREES F. | | | | | | | | | API GRAVITIES | |
|---|---|---|---|---|---|---|---|---|---|---|
| VAPOR | | | | | | | | | OBSERVED | |
| VLT | ATM EQV. | POT | PRESSURE TORR | REFLUX RATIO | CUT NO | VOL ml 60° F. | WEIGHT G | HYD RDG | TEMP ° F. | 60° F. |
| 315 | 601.4 | 350 | 5.000 | | | | START OVERHEAD | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | | MID AND | END OF RUN TRAPS | | | 20 | 17.8 | (mathematically combined) | | |
| | | | VOLUME DISTILLED | | | 2701 | | | | |
| | | | COLUMN HOLDUP | | | 4 | 4.0 | 0.0 | 0.0 | 3.4 |
| | | | BOTTOMS | | | 593 | 621.8 | 11.0 | 214.0 | 3.4 |
| | | | RECOVERED | | | 3298 | 3311.7 | | | |
| | | | FEED CHARGED | | | 3298 | 3326.3 | 18.0 | 234.0 | 8.6 |
| | | | LOSS | | | -5 | 14.6 | | | |

TABLE 3B

Distillation Report for Feedstock B-btms
(FSL #8691)
Feedstock B - Atmospheric distillation resid 650° F. + bottoms
Column Used: Sarnia HiVac

| CUT | VAPOR TEMP ST - END, ° F. | | | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|---|---|
| 1 | 601 | – | 656 | 666.4 | 639 | 4.1 | 1.0435 | 20.12 | 19.38 | 20.03 | 19.40 |
| 2 | 656 | – | 702 | 666.9 | 646 | 5.6 | 1.0321 | 20.14 | 19.59 | 20.05 | 19.62 |
| 3 | 702 | – | 752 | 334.3 | 330 | 8.3 | 1.0122 | 10.09 | 10.01 | 10.05 | 10.02 |
| 4 | 752 | – | 800 | 167.7 | 173 | 14.5 | 0.9692 | 5.06 | 5.25 | 5.04 | 5.25 |
| 5 | 800 | – | 852 | 167.3 | 181 | 21.7 | 0.9236 | 5.05 | 5.49 | 5.03 | 5.50 |
| 6 | 852 | – | 900 | 167.1 | 181 | 21.9 | 0.9224 | 5.05 | 5.49 | 5.02 | 5.50 |
| 7 | 900 | – | 950 | 238.4 | 257 | 21.2 | 0.9267 | 7.25 | 7.79 | 7.17 | 7.80 |
| 8 | 950 | – | 976 | 85.4 | 91 | 18.9 | 0.9408 | 2.58 | 2.76 | 2.57 | 2.76 |
| 9 | 976 | – | 1000 | 80.8 | 85 | 18.2 | 0.9452 | 2.44 | 2.58 | 2.43 | 2.58 |
| 10 | 1000 | – | 1026 | 93.8 | 98 | 16.9 | 0.9535 | 2.83 | 2.97 | 2.82 | 2.98 |
| COL HOLDUP | | | | 4.0 | 4 | 3.4 | 1.0489 | 0.12 | 0.12 | 0.12 | 0.12 |
| BTMS | 1026 | + | | 621.8 | 593 | 3.4 | 1.0489 | 18.78 | 17.98 | 18.69 | 18.01 |
| EOR TRAPS | | | | 17.8 | 20 | | | 0.54 | 0.61 | 0.54 | 0.61 |
| TOTALS | | | | 3311.7 | 3298 | | | 100.00 | 100.00 | 99.56 | 100.15 |
| LOSS | | | | 14.6 | –5 | | | | | 0.44 | –0.15 |
| FEED | | | | 3326.3 | 3293 | 8.6 | 1.0100 | | | 100.00 | 100.00 |
| BACK CALCULATED API & DENSITY | | | | | | 9.4 | 1.0039 | | | | |

TABLE 4

Elemental Composition of Feedstock B
Analyses on Feedstock B Atmospheric Distillation 650 + F Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 4 illustrates data from elemental analyses of Feedstock B atmospheric distillation (650+° F.) residue including some of the identified impurities. Table 4 displays the weight percent nitrogen, sulfur, nickel and vanadium present within this feedstock. These materials are removed in subsequent steps.

Step 3

The higher diamondoids enriched by the separations of Step 2 were further treated to isolate a pentamantane fraction. In one case the distillation fraction 38 of Feedstock A was passed through a silica-gel gravity liquid chromatographic column (using cyclohexane elution solvent) to remove polar compounds and asphaltenes and concentrate higher diamondoids. The use of silver nitrate impregnated silica gel (10% by weight AgNO$_3$) provides cleaner diamondoid-containing fractions by removing the free aromatic and polar components. Higher diamondoids elute in the first eluting cyclohexane fraction off the column (before aromatic hydrocarbons appeared in the column eluent column). While it is not necessary to use this chromatographic separation method, it facilitates subsequent steps.

Alternatively, pyrolysis products (as disclosed in Example 2) prepared using distillate fractions of Feedstock B could be passed through a silica-gel or AgNO$_3$ impregnated silica gel gravity liquid chromatography column to remove polar compounds and asphaltenes and concentrate higher diamondoids as described above. In either instance, the distillate fractions or the pyrolysis products could be purified using this step prior to subsequent isolation procedures.

Step 4

The eluents from the column chromatography of Steps 3 were analyzed by GC/MS to determine the GC retention times of pentamantane isomers. Individual pentamantane components with molecular weight 344 were assigned a number according to their elution order on this GC/MS analysis. This number was used to identify individual pentamantanes in subsequent steps. Note that enantiomeric pairs are not resolved in this analysis and so these enantiomeric pairs (racemic mixtures) were assigned a single number. GC Retention times vary with changing columns and GC conditions and new reference retention time tables were prepared as needed using this procedure. Below is a table used in Example 4 procedures.

| Pentamantane Reference # | 1 | 2 | 3 | 4 | 5 | 6 |
|---|---|---|---|---|---|---|
| GCMS Retention Times* (min.) | 13.68 | 15.26 | 15.31 | 15.72 | 15.85 | 16.06 |

*data from HPLC 18 (HP-5MS, 0.25 micron film, 0.25 mm I.D. × 30 m, helium carrier gas)

Step 5

A two-column preparative capillary gas chromatograph was then used to isolate pentamantanes from the distillate fractions or pyrolysis products of Step 2 cleaned-up by the column chromatography of Step 3. The cut times for the individual pentamantanes were set for the first preparative capillary GC column, methyl silicone DB-1 equivalent, using the retention times and patterns from GC/MS analysis (developed as in step 4 above). An exemplary result is shown for pentamantane #1 in FIG. 7. The pentamantane #1 containing GC peak on the first column is identified as "peak cut and sent to column 2" in FIG. 7A Material used in this isolation was a pyrolysis product of a distillate fraction from Feedstock B distillate cut #5 cleaned-up using the procedures in Step 3.

The first column was used to concentrate the pentamantane by taking a cut that was then sent to the second column.

The second column, phenyl-methyl silicone, a DB-17 equivalent, further separated the pentamantane component #1 from other materials. The material in the peak of interest identified as "peak sent to trap" was sent to GC trap fraction 6 where crystals of pentamantane component #1 accumulated (see FIG. 7B). GCMS analysis of trap #6 material (FIG. 8) showed it to be pentamantane component #1 (in the pentamantane reference GCMS retention time system set-up for this preparative GC procedure, the first eluting pentamantane component (#1) showed a retention time of 16.233 min. FIGS. 8A and B shows the high purity of pentamantane component #1 removed from GC trap fraction 6. This procedure could be repeated to isolate four other pentamantane components and three enantiomeric pairs which could be separated as described herein.

Step 6

The highly concentrated pentamantane components crystallize either directly in the trap or from solution. Under the microscope at 30×magnification, crystals of pentamantane component #1 were visible in preparative GC trap fraction 6 (see FIG. 9A). These crystals were perfectly clear and showed high refractive index. Crystals of pentamantane component #1 had never existed before this isolation. Where concentrations are not high enough for crystallization to occur, further concentration by preparative GC may be necessary. FIG. 9B is a photomicrograph of two pentamantane components that co-crystallized in a preparative GC trap.

Step 7

After obtaining crystals of suitable size, non-enantiomeric pentamantane materials could be sent for structural determination using X-ray diffraction. Enantiomeric pentamantanes can undergo further separations to resolve their two components.

Example 2

Enrichment of Pentamantanes Using Pyrolysis.

A pyrolysis method was developed to further purify distillate fractions such as distillate fractions #3–5 obtained from Feedstock B–Atmospheric distillation 650° F. +bottoms (Table 3 A/B) exploiting the great thermal stability of the pentamantanes relative to other crude oil components. FIGS. 11(A,B,C) respectively, shows the GC profile of the distillate fractions #3–5 from Feedstock B–Atmospheric distillation 650° F. +bottoms (see FIG. 10 and Table 3A&B). Removal of Nondiamondoids Using Pyrolysis This method used a reactor to pyrolyze and degrade a portion of the nondiamondoid components thereby enriching the diamondoids in the residue. Such reactors can operate at a variety of temperatures and pressures. FIGS. 12(A,B) illustrates this method and show a gas chromatogram (on a DB-17 equivalent GC column) of the Feedstock B 650° F. +distillation fraction 5 (Table 3, FIG. 10) before pyrolysis and the resulting pyrolysis product. Prior to pyrolysis, the pentamantane peaks are obscured by the presence of nondiamondoid components. Pyrolysis degraded the nondiamondoid components to easily removable gas and coke-like solids. As shown in FIG. 12B, the pentamantane peaks are clearly visible after pyrolysis.

A PARR® reactor, from PARR INSTRUMENT COMPANY, Moline, Ill., was used to process the distillation fractions obtained from vacuum distillation of a feedstock. For this example, Feedstock B 650° F. +distillation fraction 5 was used as a feedstock for pyrolysis. Pyrolysis was then conducted on 5.2 grams of this sample by heating the sample under vacuum in the reactor at 450° C. for 16.7 hours.

A comparison of the traces in FIGS. 12(A,B) show that the pyrolysis process has removed major nondiamondoid components leaving a residue enriched in pentamantane components.

Example 3

Isolation of Pentamantanes Using HPLC.

Figure 13:
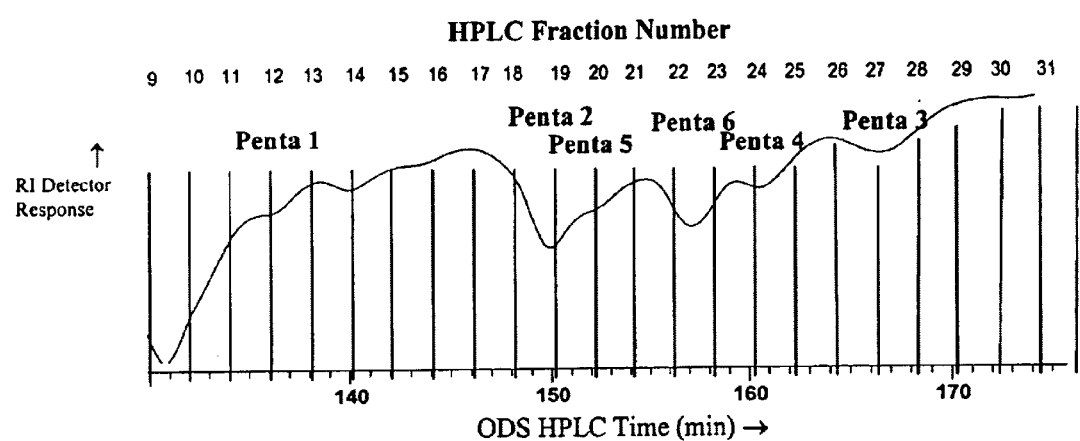
FIG. 13 illustrates the preparative HPLC Refractive Index trace (with negative polarity) of Feedstock B distillate cut pyrolysis product saturated hydrocarbon fraction showing HPLC fractions taken using octadecyl silane columns and acetone mobile phase. Pentamantanes are numbered in order of their elution on the GC/MS analyses.

In addition to the gas chromatography and pyrolysis methods described above, HPLC was also shown to provide sufficient enrichments of some pentamantanes to allow for their crystallization. In some cases, reverse-phase HPLC with acetone as mobile phase can be used to effect this purification. A preparative ODS HPLC run of Feedstock B distillate cut 5 pyrolysis product cleaned-up using procedures in Example 1, Step 3 was performed and the HPLC chromatogram recorded using a differential refractometer is shown in FIG. 13. Fractions where taken during the run as marked on FIG. 13. Each pentamantane was found by GS/MS analysis and their locations within ODS HPLC fractions marked on FIG. 13.

The HPLC columns used were two 50 cm×20 mm I.D. WHATMAN octadecyl silane (ODS) columns operated in series (Whatman columns are manufactured by Whatman Inc., USA). A 500 microliter sample of an acetone solution of the cleaned-up distillate cut 5 pyrolysis product (54 mg) was injected into the columns. The columns were setup using acetone at 5.00 ml/min as a mobile phase carrier. Some of the HPLC fractions reached the purity necessary for individual pentamantane components to crystallize from them.

Alternatively a HYPERCARB column (manufactured by Thermo Hypersil, Penn, USA) could be used to isolate and purify pentamantanes. FIG. 14 shows Hypercarb HPLC data obtained using a 10 mm I.D.×250 mm column operated with acetone at 3.00 ml/min as mobile phase (@480 psi), separating 46 mg/ml of cleaned-up distillate cut 5 pyrolysis product. FIG. 14 shows the fractions taken during the run and the location of individual pentamantane components within the fractions. These fractions were analyzed by GC/MS and the elution times of pentamantane components 1–6 are identified and marked on FIG. 14. Each pentamantane component shows a different elution time on this HPLC system and the order of elution of the pentamantane components is different from that found for ODS HPLC. The degree of separation of pentamantane components #5 and #3 (and other pentamantane components) on this HPLC is remarkable. Some of the HPLC fractions reached the purity necessary for individual pentamantane components to crystallize.

Example 4

Purification of Single Pentamantane Isomers

As shown in Example 3, pentamantanes can be isolated in high purity by using HPLC methods. In this example, combinations of HPLC columns of different specificities were used to isolate individual pentamantane components. FIG. 13 shows a preparative separation of the pentamantanes from cleaned-up distillate cut 5 pyrolysis product using an octadecyl silane (ODS) HPLC column with acetone as a mobile phase as presented in Example 3. From this run, (FIG. 13) fraction 11 was taken for further purification. This fraction contains pentamantane component #1.

Further purification of fraction 11 was achieved using a HYPERCARB stationary phase HPLC column having a different selectivity than the ODS column discussed above. FIG. 14 shows data from a Hypercarb HPLC run indicating fractions containing individual pentamantanes; fractions containing highest concentrations are marked with an "x". The differences in elution times and elution order of pentamantanes on ODS and Hypercarb HPLC are shown in FIGS. 13 and 14. Pentamantane component #1 elutes between pentamantane component #4 and pentamantane component #6 on the Hypercarb system. Pentamantane component #5 elutes first and pentamantane component #3 elutes last on Hypercarb HPLC. A 50 microliter sample of approximately 1 mg of ODS HPLC fraction 11 in acetone was injected into the Hypercarb column, 10 mm I.D.×250 mm, operated using acetone at 3.00 mL/min as mobile phase (@480 psi), and using a differential refractometer detector.

Figure 15:
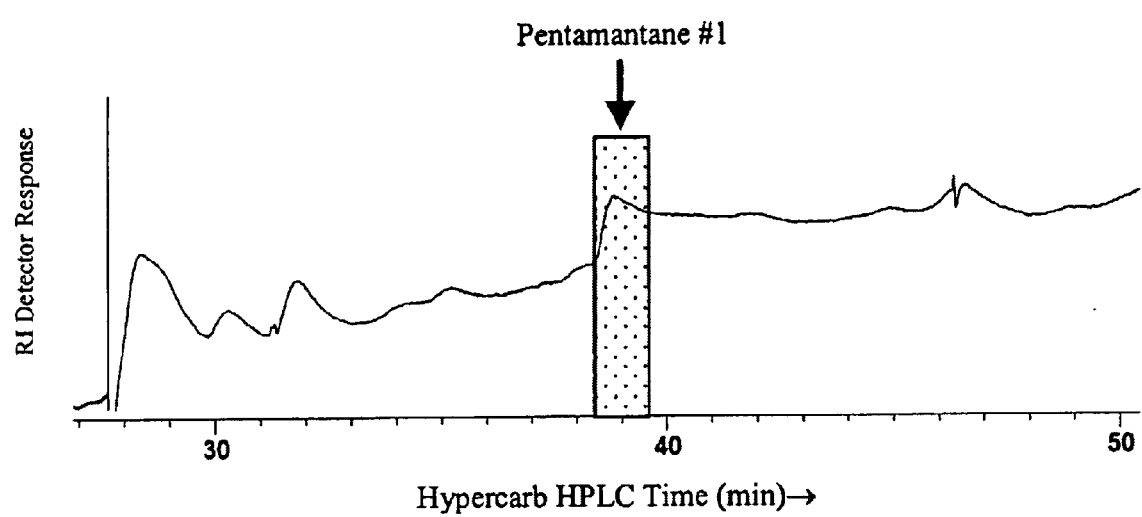
FIG. 15 illustrates the ODS HPLC chromatogram of fraction 11 (FIG. 13) run on Hypercarb stationary phase with acetone mobile phase resulting in the isolation of pentamantane component #1.
Figure 23:
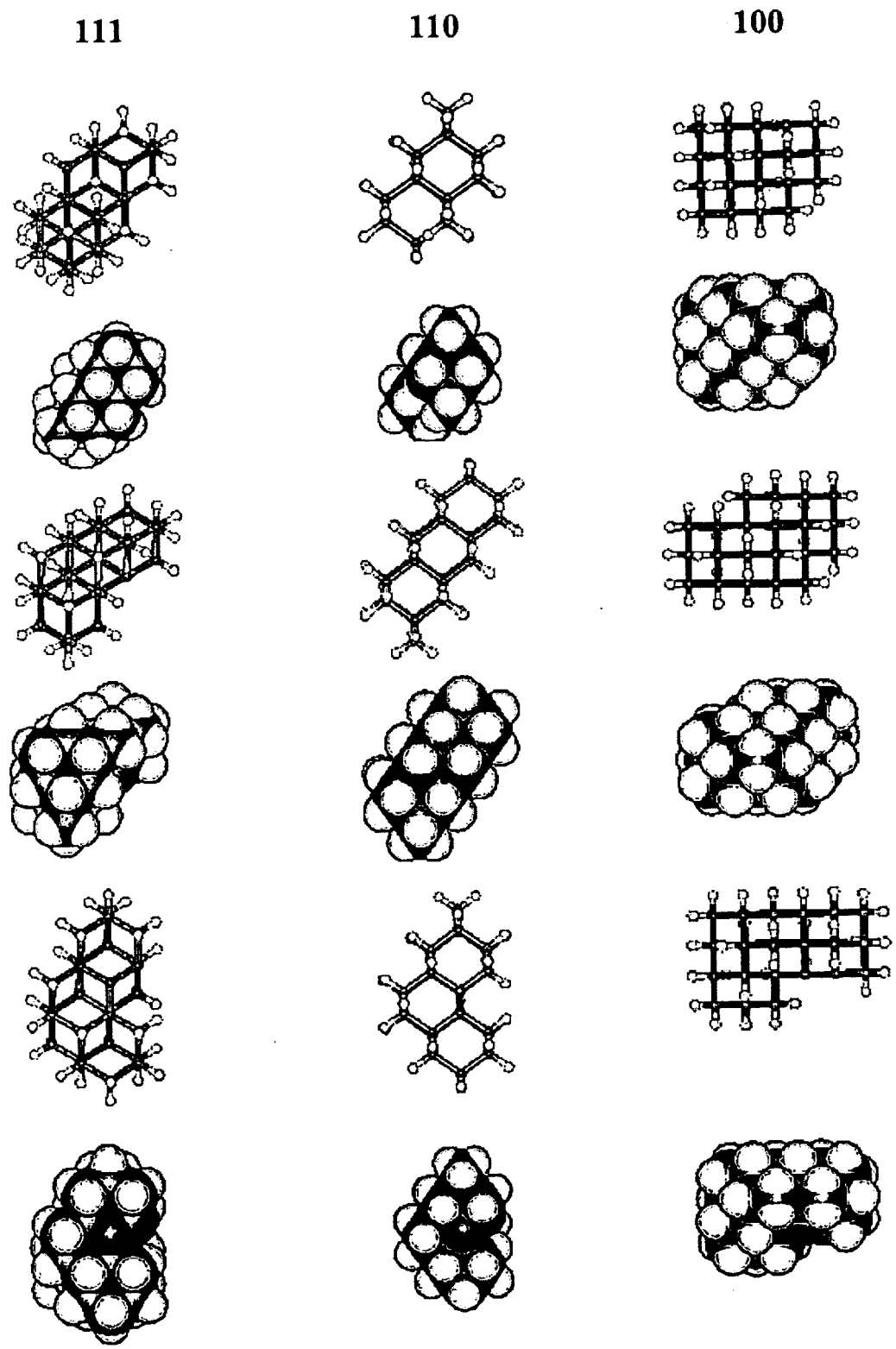
Figure 25:
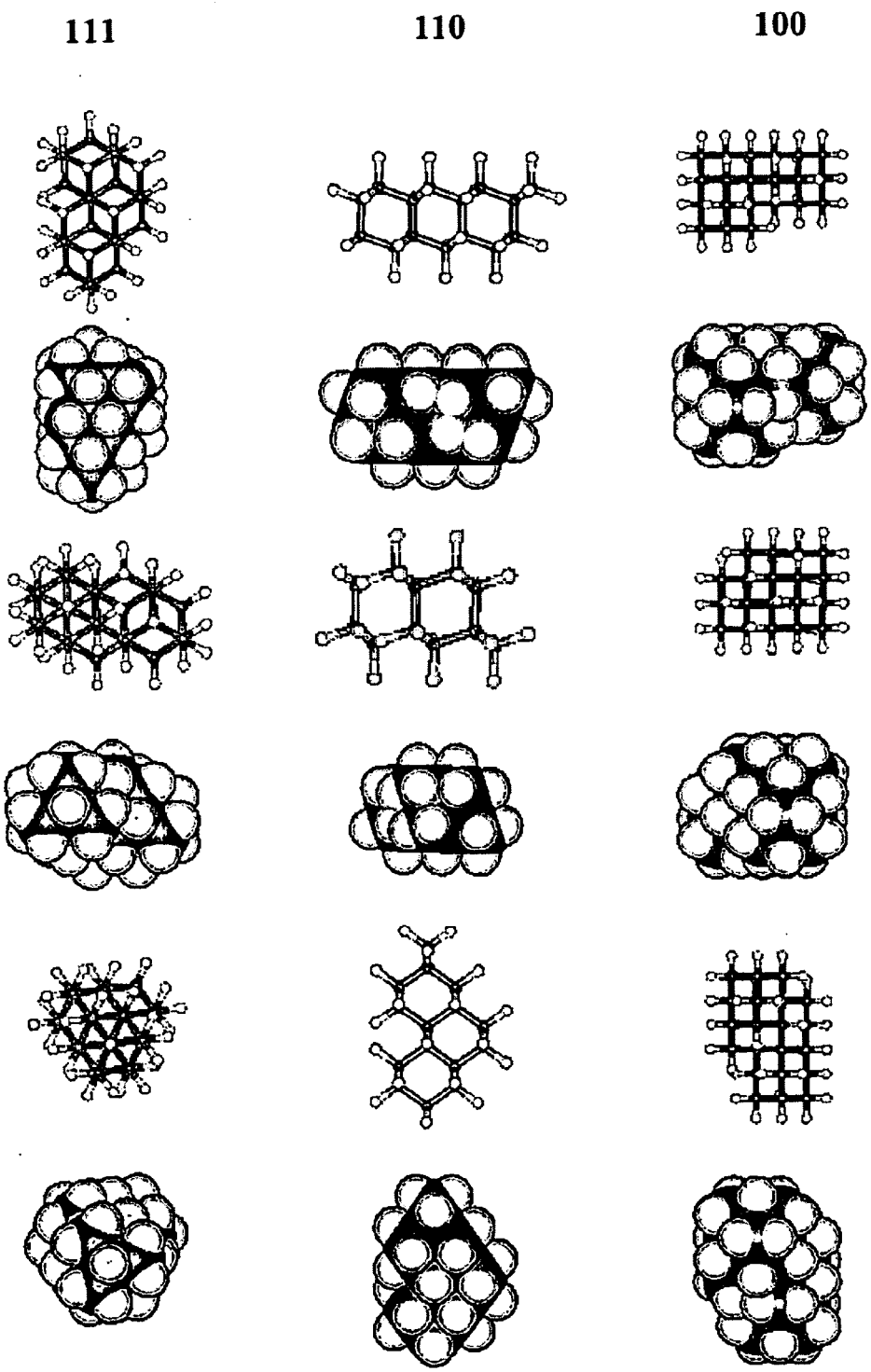
Figure 27:
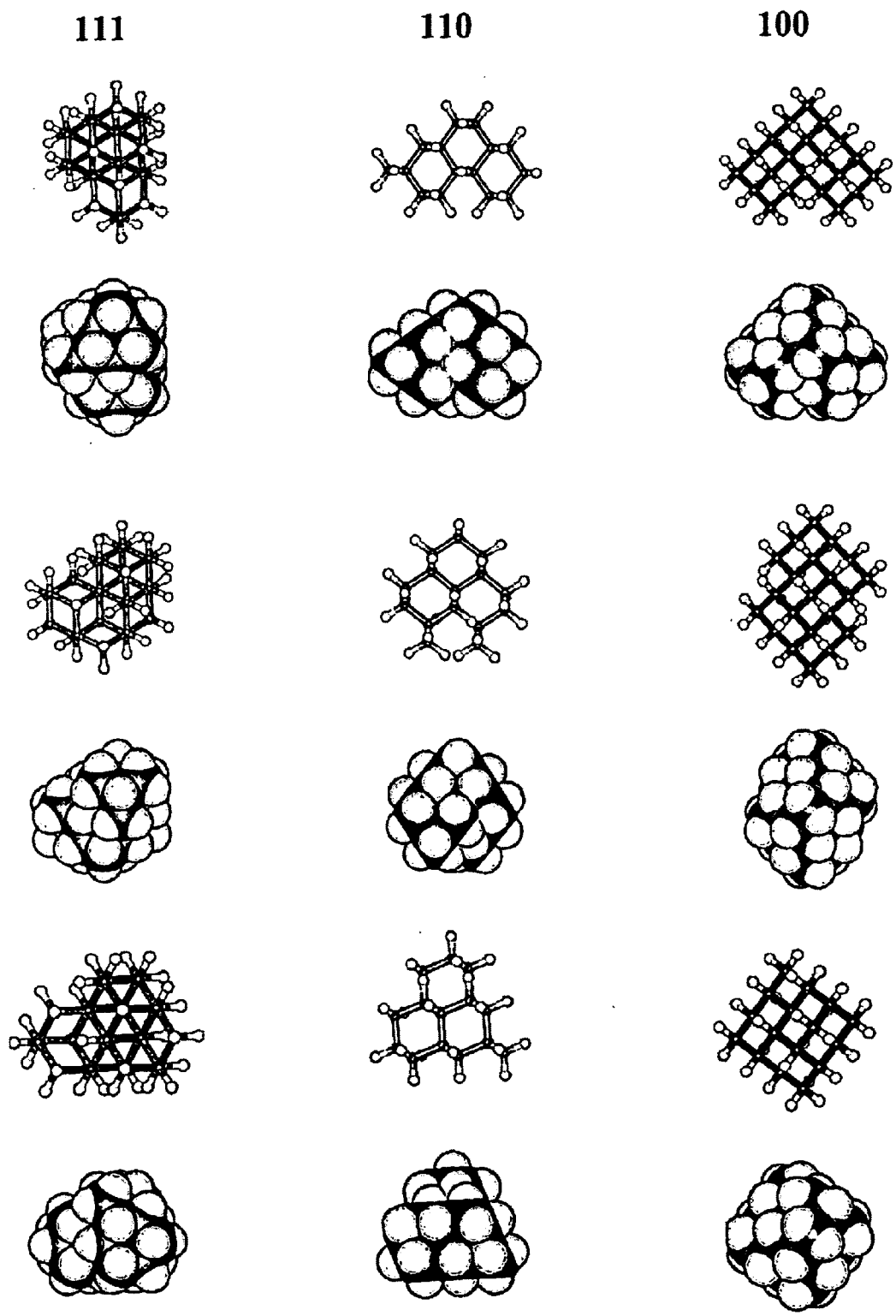
Figure 35:
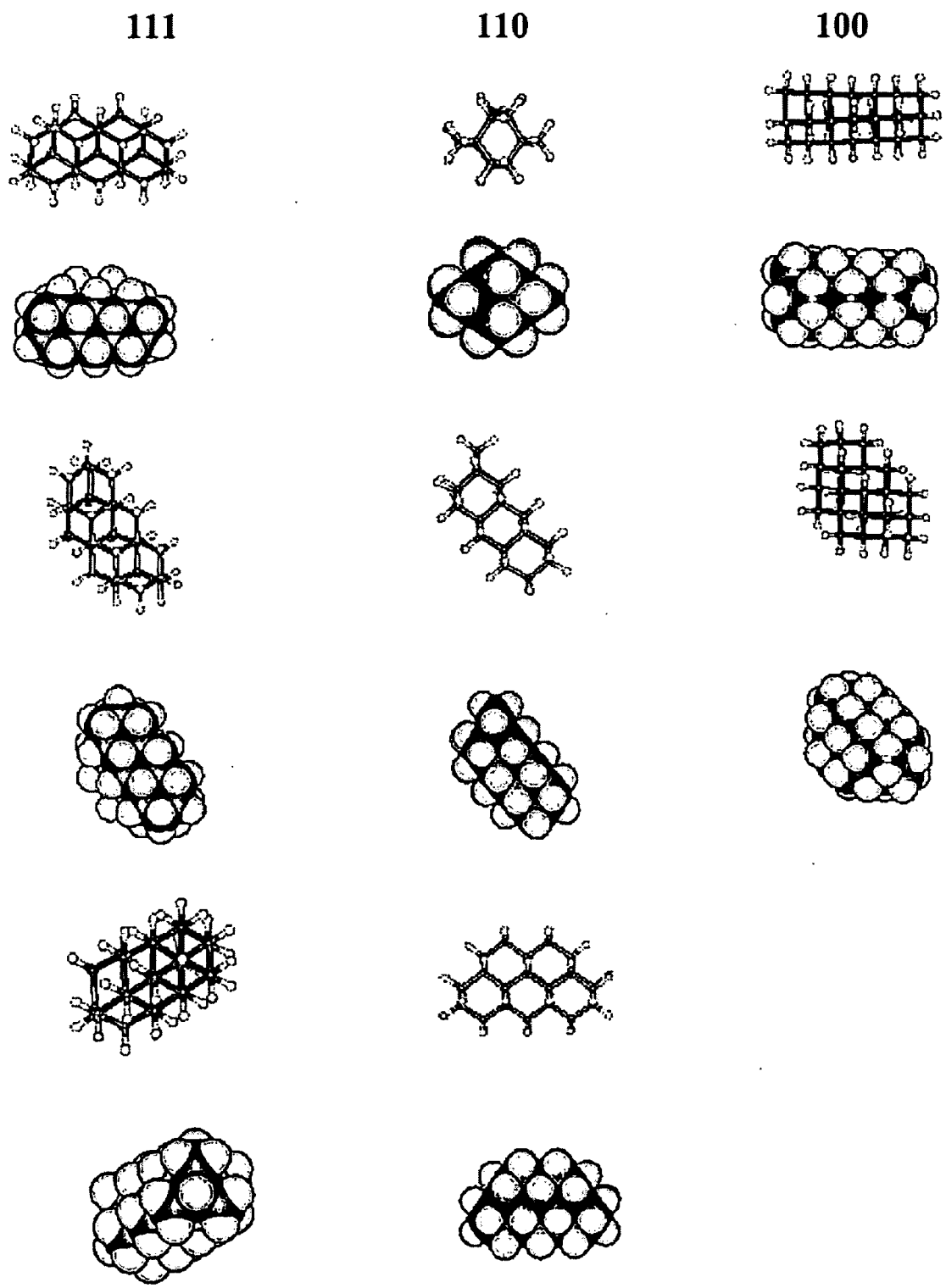
Figure 36:
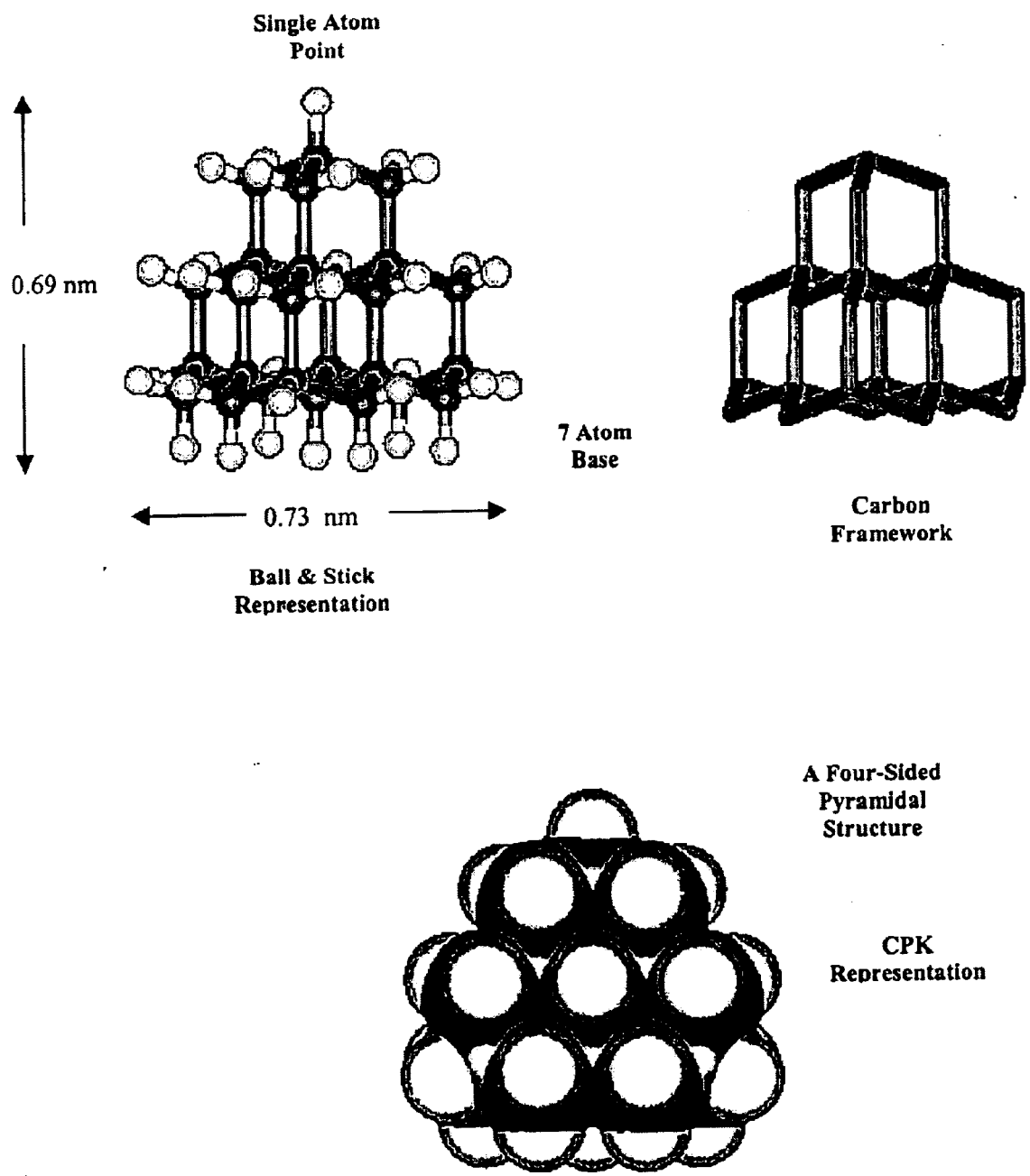

FIG. 15 shows the Hypercarb HPLC fraction cut to obtain high purity pentamantane component #1. Other pentamantane-containing ODS HPLC fractions shown in FIG. 13 were further purified using Hypercarb HPLC to isolate the remaining pentamantanes. Different separation selectivity of ODS and Hypercarb facilitates isolation of pentamantanes. The ODS and Hypercarb columns can also be used in reverse order for this isolation. FIG. 16 shows the GC/MS total ion chromatogram (TIC) of the pentamantane component #1 containing Hypercarb HPLC fraction (FIG. 15) demonstrating the high purity of the isolated pentamantane component #1. The lower half of FIG. 16 illustrates the mass spectrum of the pentamantane GC/MS peak. As indicated in FIG. 13, the various remaining ODS HPLC fractions contain other pentamantanes. By using similar methodology as above, i.e. fractionating pentamantane containing ODS fractions using the Hypercarb or other suitable column, and collecting at corresponding elution times, leads to the isolation of the remaining pentamantanes in high purity as shown in FIGS. 17–21. Specifically, FIG. 17 illustrates GC/MS total ion chromatogram (TIC) and mass spectrum of pentamantane component #2 isolated using two different HPLC columns; FIG. 18 illustrates GC/MS total ion chromatogram (TIC) and mass spectrum of pentamantane component #3 isolated using two different HPLC columns; FIG. 19 illustrates GC/MS total ion chromatogram (TIC) and mass spectrum of pentamantane component #4 isolated using two different HPLC columns; FIG. 20 illustrates GC/MS total ion chromatogram (TIC) and mass spectrum of pentamantane component #5 isolated using two different HPLC columns; and FIG. 21 illustrates GC/MS total ion chromatogram (TIC) and mass spectrum of pentamantane component #6 isolated using two different HPLC columns. The enantiomeric pentamantanes are not resolved in GS/MS and therefore, these enantiomeric pairs are referenced within a single number. These enantiomers can be separated by chiral separation methods. In addition, as previously noted, there is a condensed isomer of pentamantane having a molecular weight of 330 which is more sterically strained and this appears in lower concentrations. This pentamantane component has been observed in GC/MS analyses of distillation cut 5 pyrolysis product cleaned up using Step 3 of Example 1. This pentamantane component eluted at 14.4 minutes in the analysis of Example 1, Step 4 and could be isolated using procedures in this Example.

FIGS. 22 through 41 illustrate the size and structure with views into various diamond crystal lattice planes for ten pentamantanes.

Example 5

Purification of Substituted Pentamantane

Substituted pentamantanes are present in Feedstocks A and B. Substituted pentamantanes can be enriched from these feedstocks and purified using methodologies described for nonalkylated pentamantanes in Examples 1–4. The monomethylated pentamantane enriched in this instance has a molecular weight of 358 (yielding a mass spectrometric molecular ion of m/z 358, and shows a mass spectrometric loss of the methyl group giving the m/z 343 mass spectrometric fragment ion indicative of a pentamantane moiety (FIG. 42). This alkylated compound was enriched in ODS HPLC fraction #31 and could be further purified to form a crystal. When more than one alkylpentamantane are present, they are enriched using ODS, and/or Hypercard columns, an additional HPLC separation, or alternatively by a preparative GC procedure (as is Example 3) to yield high purity alkylpentamantanes.

What is claimed is:

1. A composition comprising diamondoids wherein at least about 25 weight percent of the diamondoids are one or more pentamantane components.

2. A composition of claim 1 wherein from 50 to 100 weight percent of the diamondoids are one or more pentamantane components.

3. A composition of claim 1 wherein from 70 to 100 weight percent of the diamondoids are one or more pentamantane components.

4. A composition of claim 1 wherein from 95 to 100 weight percent of the diamondoids are one or more pentamantane components.

5. A composition of claim 1 wherein from 99 to 100 weight percent of the diamondoids are one or more pentamantane components.

6. The composition of any of claims 1–5, wherein the one or more pentamantane components are a single pentamantane component.

7. The composition of any of claims 1–5 wherein the one or more pentamantane components are isolated optical isomers.

8. The composition of any of claims 1–5, wherein the one or more pentamantane components are isomeric pentamantane components.

9. The composition of any of claims 1–5, wherein the one or more pentamantane components is the nonisomeric pentamantane component represented by the formula $C_{25}H_{30}$.

10. The composition of any of claims 1–5 wherein the pentamantane components comprise unsubstituted pentamantane components.

11. The composition of any of claims 1–5 wherein the pentamantane components comprise substituted pentamantane components having from 1 to 10 alkyl substituents.

12. A composition comprising at least about 10% by weight of one or more pentamantane components.

13. The composition of claim 12 containing from 50 to 100% by weight of one or more pentamantane components.

14. The composition of claim 12 containing from 70 to 100% by weight of one or more pentamantane components.

15. The composition of claim 12 containing from 95 to 100% by weight of one or more pentamantane components.

16. The composition of claim 12 containing from 99 to 100% by weight of one or more pentamantane components.

17. The composition of claims 12–16 wherein the one or more pentamantane components are a single pentamantane component.

18. An enriched pentamantane component.

19. The enriched pentamantane component of claim 18 exhibiting a purity of at least 25%.

20. The enriched pentamantane component of claim 18 wherein the pentamantane component is [1231] pentamantane.

21. The enriched pentamantane component of claim 18 wherein the pentamantane component is [1213] enantiomer A pentamantane.

22. The enriched pentamantane component of claim 18 wherein the pentamantane component is [1213] enantiomer B pentamantane.

23. The enriched pentamantane component of claim 18 wherein the pentamantane component is [1234] enantiomer A pentamantane.

24. The enriched pentamantane component of claim 18 wherein the pentamantane component is [1234] enantiomer B pentamantane.

25. The enriched pentamantane component of claim 18 wherein the pentamantane component is [12(1)3] enantiomer A pentamantane.

26. The enriched pentamantane component of claim 18 wherein the pentamantane component is [12(1)3] enantiomer B pentamantane.

27. The enriched pentamantane component of claim 18 wherein the pentamantane component is [1212] pentamantane.

28. The enriched pentamantane component of claim 18 wherein the pentamantane component is [1(2,3)4] pentamantane.

29. The enriched pentamantane component of claim 18 wherein the pentamantane component is [12(3)4] pentamantane.

30. The enriched pentamantane component of claim 18 wherein the pentamantane component is an unsubstituted pentamantane component.

31. The enriched pentamantane component of claim 18 wherein the pentamantane component is a substituted pentamantane component.

32. The enriched pentamantane components of claim 31 wherein the substituted pentamantane component contains from 1 to 10 alkyl substituents.

33. The enriched pentamantane component of claim 32 wherein the substituted pentamantane component is a monomethylated pentamantane component.

34. The enriched pentamantane component of claim 18 in crystalline form.

35. A process for recovering a composition enriched in one or more pentamantane components which process comprises:
   a. selecting a feedstock comprising recoverable amounts of pentamantane components and nonpentamantane components;
   b. removing from the feedstock a sufficient amount of nonpentamantane components having boiling points less than the lowest boiling point pentamantane component under conditions to form a treated feedstock enriched in pentamantane components which can be recovered;
   c. recovering a composition enriched in one or more pentamantane components from said treated feedstock formed in b) above with one or more additional separation techniques selected from the group consisting of chromatographic techniques, thermal diffusion techniques, zone refining, progressive recrystallization and size separation techniques.

36. A process for recovering a composition enriched in pentamantane components which process comprises:
   a. selecting a feedstock comprising recoverable amounts of pentamantane components and nonpentamantane components including nondiamondoid components;
   b. removing from the feedstock a sufficient amount of nonpentamantane components having a boiling point less than the lowest boiling point pentamantane component under conditions to form a treated feedstock enriched in pentamantane components which can be recovered;
   c. thermally degrading said treated feedstock to pyrolyze at least a sufficient amount of nondiamondoid components therefrom under conditions to form a thermally treated feedstock retaining recoverable amounts of pentamantane;
   d. recovering a composition enriched in one or more pentamantane components from said thermally treated feedstock formed in c) above with one or more additional separation techniques selected from the group consisting of chromatographic techniques, thermal diffusion techniques, zone refining, progressive recrystallization and size separation techniques.

37. A process for recovering a composition enriched in one or more pentamantane components which process comprises:
   a. selecting a feedstock comprising recoverable amounts of pentamantane components and nonpentamantane components including nondiamondoid components;
   b. thermally degrading said feedstock to pyrolyze at least a sufficient amount of nondiamondoid components therefrom under conditions to provide a thermally treated feedstock retaining recoverable amounts of pentamantane;
   c. removing from the thermally treated feedstock a sufficient amount of nonpentamantane components having a boiling point less than the lowest boiling point of pentamantane component under conditions to form a treated feedstock enriched in pentamantanes components which can be recovered;
   d. recovering a composition enriched in one or more pentamantane components from said treated feedstock recovered in c) above with one or more additional separation techniques selected from the group consisting of chromatographic techniques, thermal diffusion techniques, zone refining, progressive recrystallization and size separation techniques.

38. A process for recovering a composition enriched in one or more pentamantane components which process comprises:
   a. selecting a feedstock comprising recoverable amounts of pentamantane components and nonpentamantane components;
   b. fractionating the feedstock to form one or more cuts enriched in materials having boiling points in the range of from just below the boiling point of the lowest boiling pentamantane component to just above the boiling point of the highest boiling pentamantane component;
   c. recovering a composition enriched in one or more pentamantane components from said one or more cuts formed in b) above with one or more additional separation techniques selected from the group consisting of chromatographic techniques, thermal diffusion techniques, zone refining, progressive recrystallization and size separation techniques.

39. A process for recovering a composition enriched in one or more pentamantane components which process comprises:
   a. selecting a feedstock comprising recoverable amounts of pentamantane components and nonpentamantane components including nondiamondoid components;

b. fractionating the feedstock to form one or more cuts enriched in materials having boiling points in the range of from just below the boiling point of the lowest boiling pentamantane component to just above the boiling point of the highest boiling pentamantane component;

c. thermally degrading one or more cuts said to pyrolyze at least a sufficient amount of nondiamondoid components therefrom under conditions to form one or more thermally treated cuts retaining recoverable amounts of pentamantane;

d. recovering a composition comprising one or more pentamantane components from one or more said thermally treated cuts formed in c) above with one or more additional separation techniques selected from the group consisting of chromatographic techniques, thermal diffusion techniques, zone refining, progressive recrystallization and size separation techniques.

40. A process for recovering a composition enriched in one or more pentamantane components which process comprises:

a. selecting a feedstock comprising recoverable amounts of pentamantane components and nonpentamantane compounds including nondiamondoid components;

b. thermally degrading said feedstock to pyrolyze at least a sufficient amount of nondiamondoid components therefrom under conditions to provide a thermally treated feedstock retaining recoverable amounts of pentamantane;

c. fractionating the thermally treated feedstock to form one or more cuts enriched in materials having boiling points in the range of from just below the boiling point of the lowest boiling pentamantane component to just above the boiling point of the highest boiling pentamantane component;

d. recovering a composition enriched in one or more pentamantane components from one or more cuts formed c) above with one or more additional separation techniques selected from the group consisting of chromatographic techniques, thermal diffusion techniques, zone refining, progressive recrystallization and size separation techniques.

41. The process according to any of claims 38–40 wherein said boiling point range is a range having atmospheric equivalents of between about 330 to about 490° C.

42. The process according to any of claims 35–40 wherein said separation technique is a chromatographic technique.

43. The process according to claim 42 wherein said chromatographic technique is selected from the group consisting of liquid chromatography, preparative gas chromatography and high performance liquid chromatography.

44. The process according to claim 42 wherein said additional separation technique is high performance liquid chromatography comprising one or more high performance liquid chromatography columns.

45. The process according to claim 44 wherein the high performance liquid chromatography columns are selected to have a different specificity to the pentamantane components.

46. A product prepared by the process of claim 35.
47. A product prepared by the process of claim 36.
48. A product prepared by the process of claim 37.
49. A product prepared by the process of claim 38.
50. A product prepared by the process of claim 39.
51. A product prepared by the process of claim 40.

* * * * *